United States Patent
Wang et al.

(10) Patent No.: US 11,096,928 B2
(45) Date of Patent: Aug. 24, 2021

(54) PHARMACEUTICAL COMPOSITION

(71) Applicant: WUHAN LL SCIENCE AND TECHNOLOGY DEVELOPMENT CO., LTD., Hubei (CN)

(72) Inventors: Chaodong Wang, Hubei (CN); Yongkai Chen, Hubei (CN); Liu Hu, Hubei (CN); Xian Zeng, Hubei (CN); Daiwu Kang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 1 day.

(21) Appl. No.: 16/340,035

(22) PCT Filed: Sep. 27, 2017

(86) PCT No.: PCT/CN2017/103651
§ 371 (c)(1),
(2) Date: Apr. 5, 2019

(87) PCT Pub. No.: WO2018/064945
PCT Pub. Date: Apr. 12, 2018

(65) Prior Publication Data
US 2020/0038379 A1    Feb. 6, 2020

(30) Foreign Application Priority Data

Oct. 8, 2016 (CN) .......................... 201610887841.8

(51) Int. Cl.
| | | |
|---|---|---|
| *A61K 31/4245* | (2006.01) | |
| *A61K 31/222* | (2006.01) | |
| *A61K 31/41* | (2006.01) | |
| *A61P 9/12* | (2006.01) | |
| *A61K 31/496* | (2006.01) | |

(52) U.S. Cl.
CPC ........ *A61K 31/4245* (2013.01); *A61K 31/222* (2013.01); *A61K 31/41* (2013.01); *A61K 31/496* (2013.01); *A61P 9/12* (2018.01)

(58) Field of Classification Search
CPC ................ A61K 31/192; A61K 31/197; A61K 31/4164; A61K 31/497; A61K 31/216; A61K 31/222; A61K 31/41; A61K 31/4245; A61K 31/496; A61K 31/504; A61K 31/501; A61P 9/04; A61P 9/12
See application file for complete search history.

(56) References Cited

U.S. PATENT DOCUMENTS

| | | | | |
|---|---|---|---|---|
| 2005/0187269 A1* | 8/2005 | Kuroita | ..................... | A61P 9/10 514/364 |
| 2005/0288272 A1* | 12/2005 | Ziegler | .................. | A61K 45/06 514/212.07 |
| 2019/0177312 A1* | 6/2019 | Lei | ............................ | A61P 9/12 |

FOREIGN PATENT DOCUMENTS

| | | | | |
|---|---|---|---|---|
| CN | 1615134 A | | 5/2005 | |
| CN | 1946717 A | | 4/2007 | |
| CN | 103709154 A | | 4/2014 | |
| CN | 104774196 A | * | 7/2015 | |
| CN | 105693543 A | | 6/2016 | |
| CN | 105837464 A | | 8/2016 | |
| EP | 0498361 A2 | * | 8/1992 | ............. A61K 45/06 |
| WO | WO-2007056324 A2 | * | 5/2007 | ............. A61K 45/06 |
| WO | WO-2018010622 A1 | * | 1/2018 | ................ A61P 9/12 |

OTHER PUBLICATIONS

English translation of CN-104774196-A, publ Jul. 15, 2015 (Year: 2015).*

* cited by examiner

*Primary Examiner* — Sarah Pihonak
(74) *Attorney, Agent, or Firm* — Novick, Kim & Lee, PLLC; Allen Xue

(57) ABSTRACT

The present invention relates to a pharmaceutical composition comprising: (a) at least one neutral endopeptidase inhibitor or a pharmaceutically acceptable salt or ester thereof, (b) at least one compound represented by formula (I) or a pharmaceutically acceptable salt or ester thereof, and a pharmaceutically acceptable carrier. Combined administration showed better medicinal effects than separate administration.

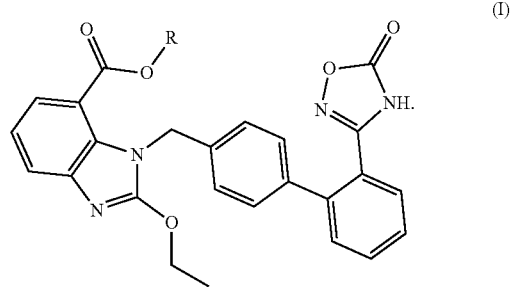

13 Claims, 4 Drawing Sheets

PHARMACEUTICAL COMPOSITION

FIELD OF THE INVENTION

Embodiments of the present disclosure relate to the field of medicine, and specifically relates to a pharmaceutical composition comprising a neutral endopeptidase (NEP) inhibitor and an azilsartan medoxomil derivative.

BACKGROUND OF THE INVENTION

Cardiovascular disease, also known as circulatory disease, refers to a series of circulatory diseases. The circulatory system mainly includes the heart and blood vessels (arteries, veins, microvessels). According to statistics, cardiovascular disease is the number one cause of death worldwide. Cardiovascular diseases cause more deaths each year than any other cause of death. Common cardiovascular diseases include: hypertension, heart failure, coronary heart disease, heart disease, atherosclerosis, angina pectoris, left ventricular dysfunction, hypertrophic cardiomyopathy, diabetic cardiomyopathy, supraventricular and ventricular arrhythmia, housing tremor, cardiac fibrosis, atrial flutter, harmful vascular remodeling, myocardial infarction and its sequelae. Cardiovascular diseases generally have similar causes, pathogenesis, and treatments. Most cardiovascular diseases can be prevented by handling risk factors such as tobacco use, unhealthy diet, obesity, high blood pressure, diabetes, and elevated blood lipids.

The World Health Organization believes that by combined application of drugs such as cholesterol-lowering statins, blood pressure lowering drugs and aspirin, the risk of cardiovascular recurrence or death can be significantly reduced. However, optional combination of cardiovascular disease drugs with different mechanisms of action does not necessarily lead to a beneficial effect. Therefore, pharmaceutical compositions that can exert combined therapeutic effects are developed to provide more effective prevention and treatment on cardiovascular diseases.

Neutral endopeptidase (NEP) is a zinc metalloproteinase on the surface of endothelial cells. Inhibition of NEP increases atrial natriuretic peptide (ANP), brain natriuretic peptide (BNP), C-type natriuretic peptide (CNP), bradykinin and adrenomedullin levels, thus playing a role in diuresis, vasodilation, improvement of endothelium dilation and inhibition of proliferation of vascular smooth muscle cells under pathological conditions, further improving vascular hemodynamics, preventing atherosclerosis, and delaying the progression of heart failure.

Angiotensin II (Ang II) is an important regulator for dynamic balance of body fluids, involving balance of blood pressure, electrolyte and the like. It has been confirmed by a large number of literatures that Ang II plays a major role in the pathogenesis of hypertension, arterial disease, cardiac hypertrophy, heart failure, diabetes and kidney disease. Since the abnormal increase of Ang II level is directly related to the occurrence and development of hypertension, cardiac hypertrophy, heart failure and the like, blocking the binding of Ang II to its specific receptor therefore contributes to the protection of heart and blood vessels. It has been proved by numerous randomized clinical trials that Angiotensin Receptor Blockers (ARB) is effective in reducing cardiovascular mortality and morbidity. Angiotensin Receptor Blockers (ARB) has been widely used in hypertension as well as prevention and treatment of other heart and kidney diseases abroad. In terms of structure, ARB for current clinical application can be divided into two types: (1) biphenyl tetrazolium, including losartan, valsartan, irbesartan, candesartan cilexetil and azilsartan medoxomil; (2) non-biphenyltetrazolium, including eprosartan and telmisartan).

Chinese Patent Application No. CN1615134A discloses a pharmaceutical composition comprising valsartan or a pharmaceutically acceptable salt thereof and a NEP inhibitor or a pharmaceutically acceptable salt thereof; Chinese Patent Application CN105693543A discloses a pharmaceutical composition comprising a NEP inhibitor sacubitril (AHU 377, CAS No. 149709-62-6) salt, a pharmaceutical excipient and an AT1 receptor antagonist such as losartan, eprosartan, valsartan, irbesartan and the like or a pharmaceutically acceptable salt thereof. Chinese patent application CN105837464A discloses a pharmaceutical composition comprising a NEP inhibitor containing sacubitril sodium, a pharmaceutical excipient and another active ingredient such as losartan, eprosartan, valsartan, irbesartan and the like or a pharmaceutically acceptable salt thereof.

Chinese Patent Application (Publication No. CN103709154A) discloses a compound of formula (I) for the first time:

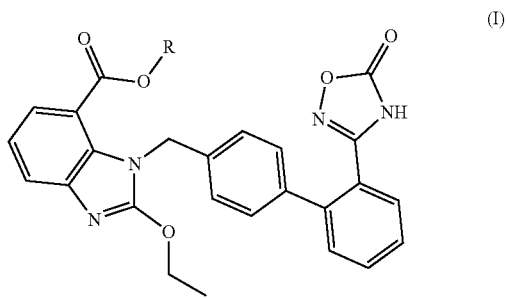

The above compound is a sartan drug which is coupled with ligustrazine or NO donor and is a prodrug of angiotensin II receptor antagonist azisartan (TAK-536). The above compound releases hydroxyligustrazine or NO in vivo, which makes an effective synergistic action with azilsartan, accordingly enhancing its antihypertensive effect as well as contributing to reduction of heart rate and adverse effect, and further bringing desired protective effects to patients' hearts and kidneys. A potassium salt of compound (I), represented by the chemical formula (II) as below, which has been discovered by the inventors of the present specification, has better solubility, higher bioavailability, more potent and longer-lasting antihypertensive effect, more obvious and sustainable effect of lowering heart rate, higher safety, as well as desired protective effect on the heart and kidney function of patients, and can be used for preventing and/or treating hypertension, chronic heart failure, diabetic nephropathy, and the like.

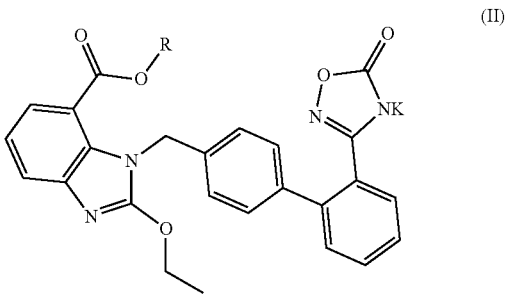

SUMMARY OF THE INVENTION

It has been found by inventors of the present invention that unexpected synergistic effects are achieved by combination of a neutral endopeptidase inhibitor or a pharmaceutically acceptable salt or ester thereof with an angiotensin II receptor antagonist of the formula (I) or a pharmaceutically acceptable salt or ester thereof. The above combination significantly enhances the efficacy of any single active component, and shows more stable and longer-lasting hypotensive effect as well as more obvious and longer-lasting heart reduction, and at the same time, improves heart function significantly and effectively treats acute and chronic heart failure. In addition, by way of combination, lower dosage or lower administration frequency of the drug is demand for desired effect and side effect of a single drug is reduced.

An embodiment of the present disclosure provides a pharmaceutical composition, which comprises: (a) at least one neutral endopeptidase inhibitor or pharmaceutically acceptable salt or ester thereof; (b) at least one compound of formula (I) as follows, or pharmaceutically acceptable salt or ester thereof; and a pharmaceutically acceptable carrier:

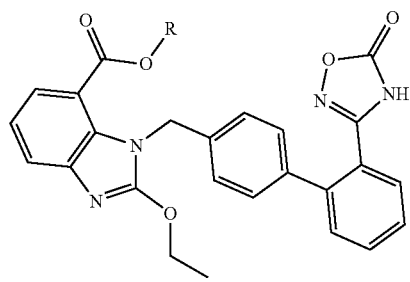
(I)

wherein, R represents

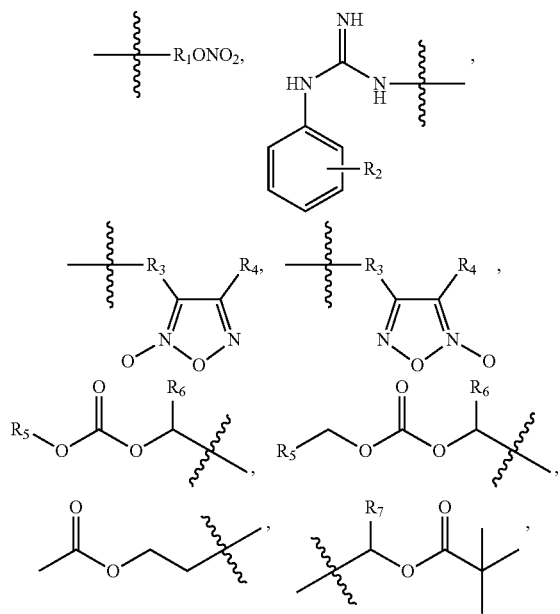

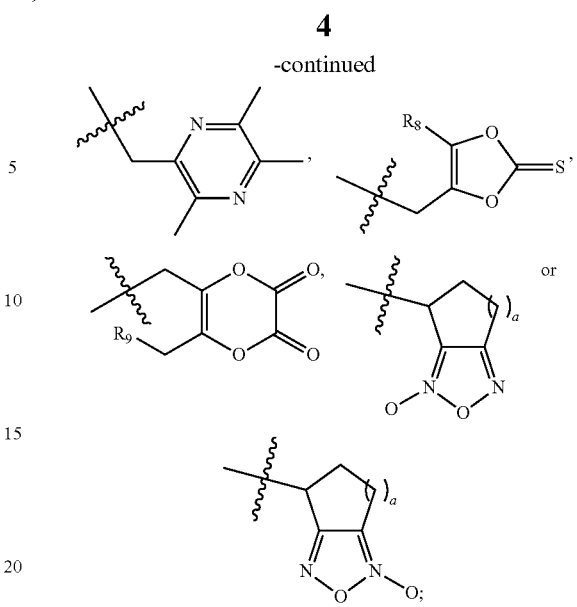

each a is same or different, and is independently selected from 0, 1, 2, 3, 4, 5 or 6;

$R_1$ represents a substituted or unsubstituted group selected from: $C_1$-$C_8$ alkyl, $C_2$-$C_8$ alkenyl, $C_2$-$C_8$ alkynyl,

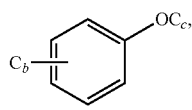

$(CH_2)_nO(CH_2)_m$,

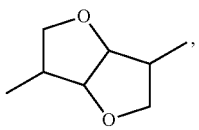

aryl or heteroaryl, wherein, each of b and c in

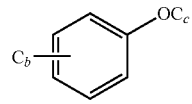

represents a number of carbon atoms in the alkyl chain, and is independently selected from 0, 1, 2, 3, 4, 5 or 6, and each of n and m in $(CH_2)_nO(CH_2)_m$ is independently selected from 1, 2, 3, 4, 5 or 6;

$R_2$ represents hydrogen, halogen, nitro, cyano, or a substituted or unsubstituted group selected from: $C_1$-$C_8$ alkoxy, $C_1$-$C_8$ alkyl, $C_1$-$C_8$ alkylsulfonylamino, arylsulfonylamino, heteroaryl sulfonylamino, aminosulfonyl and amino;

$R_3$ represents null or a substituted or unsubstituted group selected from:

$C_1$-$C_8$ alkyl, $C_1$-$C_8$ alkoxy, $C_2$-$C_8$ alkeneoxy, $C_2$-$C_8$ alkyneoxy, $C_1$-$C_6$ alkoxy —$C_1$-$C_6$ alkyl,

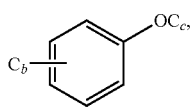

aryl and heteroaryl, wherein, each of b and c in

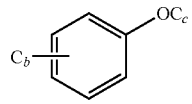

represents a number of carbon atoms in the alkyl chain, and is independently selected from 0, 1, 2, 3, 4, 5 or 6;

$R_4$ represents cyano, or a substituted or unsubstituted group selected from: aryl, arylsulfonyl, heteroaryl, $C_1$-$C_8$ alkoxy, $C_1$-$C_8$ nitrate, $C_1$-$C_8$ alkyl;

$R_5$ represents cyano, or a substituted or unsubstituted group selected from: aryl, heteroaryl, $C_1$-$C_8$ alkoxy, $C_1$-$C_8$ nitrate, $C_1$-$C_8$ alkyl, $C_1$-$C_8$ alkenyl, $C_1$-$C_8$ alkynyl,

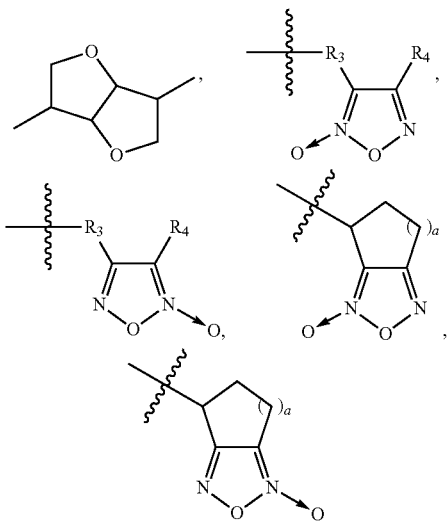

and $(CH_2)_nO(CH_2)_m$, wherein $R_3$, $R_4$, a, m and n are as defined above; each of $R_6$ and $R_7$ independently represents hydrogen, substituted or unsubstituted $C_1$-$C_8$ alkoxy or $C_1$-$C_8$ alkyl;

each of $R_8$ and $R_9$ independently represents hydrogen, substituted or unsubstituted $C_1$-$C_8$ alkoxy, $C_1$-$C_8$ nitrate or $C_1$-$C_8$ alkyl.

An embodiment of the present disclosure provides a pharmaceutical kit comprising separate containers, wherein, a first container of the containers comprises: (a) a first pharmaceutical composition comprising a first pharmaceutically acceptable carrier, and at least one neutral endopeptidase inhibitor or pharmaceutically acceptable salt or ester thereof; and a second container of the containers comprises: (b) a second pharmaceutical composition comprising a second pharmaceutically acceptable carrier, and at least one compound of formula (I), or pharmaceutically acceptable salt or ester thereof.

According to an embodiment of the present disclosure, use of the above pharmaceutical composition or pharmaceutical kit for preparing a medicament for preventing and/or treating cardiovascular diseases is provided.

According to an embodiment of the present disclosure, use of the above pharmaceutical composition or pharmaceutical kit for prevention and/or treatment of cardiovascular diseases is provided.

According to an embodiment of the present disclosure, use of an NEP inhibitor or pharmaceutically acceptable salt or ester thereof for preparing a medicament combining a compound of formula (I) or pharmaceutically acceptable salt or ester thereof for preventing and/or treating cardiovascular diseases, is provided.

According to an embodiment of the present disclosure, use of a compound of formula (I) or pharmaceutically acceptable salt or ester thereof for preparing a medicament combining a NEP inhibitor or pharmaceutically acceptable salt or ester thereof for preventing and/or treating cardiovascular diseases is provided.

According to another embodiment of the present disclosure, a method for preventing and/or treating cardiovascular diseases is provided, which comprises administering to a patient in need at least one neutral endopeptidase inhibitor or pharmaceutically acceptable salt or ester thereof, and at least one compound of formula (I) or pharmaceutically acceptable salt or ester thereof. It will be understood by those skilled in the art that the above-mentioned at least one neutral endopeptidase inhibitor or pharmaceutically acceptable salt or ester thereof and at least one compound of formula (I) or pharmaceutically acceptable salt or ester thereof may be administered simultaneously, sequentially, or at appropriate intervals, as needed, in form of a single preparation or separate preparations, to the patients in need.

DEFINITION AND EXPLANATION OF TERMS

Unless otherwise indicated, the definitions of groups and terms in the present specification and claims, including definitions as examples, exemplary definitions, preferred definitions, definitions described in tables, definitions of specific compounds in examples, can be in any combination or association with each other. Such combined and associated group definitions and compound structures should fall within the (protection) scope of the description of the present application.

Whenever a numerical range recited in the specification and claims herein is defined as "an integer", it should be understood that both endpoints of the range and each integer within the range are recited. For example, "an integer of 0 to 10" should be understood as reciting each integer of 0, 1, 2, 3, 4, 5, 6, 7, 8, 9 and 10. When the numerical range is defined as "a number", it should be understood that both endpoints of the range, each integer within the range, and each decimal within the range are recited. For example, "a number from 0 to 10" should be understood as not only each integer of 0, 1, 2, 3, 4, 5, 6, 7, 8, 9, and 10, but also at least the sum of each of the integers and 0.1, 0.2, 0.3, 0.4, 0.5, 0.6, 0.7, 0.8, and 0.9, respectively, are recited.

The term "one or more" refers to one or more than one. For example, the term "one or more" includes but is not limited to 1, 2, 3, 4, 5, 6, 7, 8, 9 or 10.

The term "halogen" refers to F, Cl, Br, and I in this specification.

"Substituted" means being substituted with one or more optional substituents. Suitable substituents include, but are not limited to, halogen, amino, cyano, nitro, carbonyl (oxo), decyl (thio), hydroxy, ether, carboxy, alkyl, alkoxy, alkenyl, alkynyl, alkenyloxy, alkynyloxy, aryl, heteroaryl, cycloalkyl, heterocyclyl, substituted acyl, substituted sulfonyl, substituted ester, —CH=CHCO$_2$H, —CH=CHCO$_2$ alkyl. The substituents may be unsubstituted or further optionally substituted by one or more substituents which may be same or different selected from the above.

"Alkyl" alone or as a suffix or prefix as used herein refers to branched or linear saturated aliphatic hydrocarbon groups with 1 to 20 carbon atoms (or with a specific number of carbon atoms if the specific number is provided). For example, "$C_1$-$C_8$ alkyl" refers to a linear or branched alkyl group having 1, 2, 3, 4, 5, 6, 7 or 8 carbon atoms. Examples of the "alkyl" include, but are not limited to, methyl, ethyl, n-propyl, isopropyl, n-butyl, isobutyl, sec-butyl, tert-butyl, pentyl and hexyl. When an alkyl is substituted by a substituent, it includes an alkyl substituted with one or more halogens, for example, an alkyl substituted with 1, 2, 3, 4, 5 or 6 halogens. For example, the alkyl is a trifluoromethyl group.

"Alkenyl" alone or as a suffix or prefix as used herein refers to branched or linear aliphatic hydrocarbon with 2 to 20 carbon atoms (or with a specific number of carbon atoms if the specific number is provided) containing an alkenyl or olefin. For example, "$C_2$-6 alkenyl" refers to an alkenyl group having 2, 3, 4, 5 or 6 carbon atoms. Examples of alkenyl groups include, but are not limited to, vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

"Alkynyl" alone or as a suffix or prefix as used herein refers to branched or linear aliphatic hydrocarbon with 2 to 20 carbon atoms (or with a specific number of carbon atoms if the specific number is provided) containing an alkynyl or alkyne. For example, ethynyl, propynyl (e.g., 1-propynyl, 2-propynyl), 3-butynyl, pentynyl, hexynyl, and 1-methyl-pent-2-ynyl.

"Aryl" as used herein refers to an aromatic ring comprising 5 to 20 carbon atoms. For example, the term "aryl" refers to an aromatic ring containing 5, 6, 7 or 8 carbon atoms which may be a monocyclic aromatic group such as a phenyl group; or, the term "aryl" refers to a ring comprising 8, 9, 10, 11, 12, 13 or 14 carbon atoms which may be a polycyclic structure such as naphthyl. The aromatic ring may be further substituted with one or more of the above substituents at one or more positions. The term "aryl" also includes polycyclic ring systems having two or more rings with two or more carbon atoms shared by two adjacent rings ("fused ring"), wherein at least one ring is aromatic and the other ring(s) may be, for example, a cycloalkyl, cycloalkenyl, cycloalkynyl, aryl and/or heterocyclic group. Examples of polycyclic rings include, but are not limited to, 2,3-dihydro-1,4-benzodioxadiene and 2,3-dihydro-1-benzofuran.

"Cycloalkyl" as used herein refers to saturated cyclic groups having a specified number of carbon atoms. This term may be fused or bridged polycyclic systems. A cycloalkyl group may have 3 to 40 carbon atoms in its ring structure. In an embodiment, the cycloalkyl has 3, 4, 5 or 6 carbon atoms in its ring structure. For example, "$C_{3-6}$ cycloalkyl" refers to a group such as cyclopropyl, cyclobutyl, cyclopentyl or cyclohexyl.

As used herein, "heteroaryl" refers to a heteroaromatic ring having at least one heterocyclic atom such as sulfur, oxygen or nitrogen. The heteroaryl groups include monocyclic systems and polycyclic systems (e. g., having 2, 3 or 4 fused rings). Examples of the heteroaryl groups include, but are not limited to, pyridyl, pyrimidinyl, pyrazinyl, pyridazinyl, triazinyl, furyl, quinolyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl, oxazolyl, 1,2,4-thiadiazolyl, isothiazolyl, benzothiophenyl, purinyl, carbazolyl, benzimidazolyl, benzoxazolyl, azabenzoxazolyl, imidazothiazolyl, benzo[1,4]dioxinyl, benzo[1,3]dioxolyl and the like. In some embodiments, the heteroaryl has 3 to 40 carbon atoms and in other embodiments 3 to 20 carbon atoms. In some embodiments, the heteroaryl contains 3 to 14, 4 to 14, 3 to 7, or 5 to 6 ring-forming atoms. In some embodiments, the heteroaryl has 1 to 4, 1 to 3 or 1 to 2 heteroatoms. In some embodiments, the heteroaryl has one heteroatom.

Unless otherwise indicated, the term "heterocyclyl" as used herein refers to a saturated, unsaturated or partially saturated monocyclic, bicyclic or tricyclic ring containing from 3 to 20 atoms, wherein 1, 2, 3, 4 or 5 ring atoms are selected from nitrogen, sulfur or oxygen; and unless otherwise indicated, the ring atoms may be connected via carbon or nitrogen, wherein the —$CH_2$— group is optionally substituted by —C(O)—; and unless otherwise stated, the ring nitrogen atom or the ring sulfur atom is optionally oxidized to form an N-oxide or S-oxide, or the cyclic nitrogen atom is optionally quaternized; wherein —NH in the ring is optionally substituted by acetyl, formyl, methyl or methanesulfonyl; and the ring is optionally substituted with one or more halogens. It should be understood that when a total number of S atoms and O atoms in the heterocyclic group exceeds 1, these hetero atoms are not adjacent to each other. If the heterocyclyl is bicyclic or tricyclic, at least one ring of the heterocyclyl may be optionally a heteroaromatic or aromatic ring, provided that at least one ring is non-heteroaromatic. If the heterocyclyl is a monocyclic ring, the heterocyclyl must not be aromatic. Examples of the heterocyclyl include, but are not limited to, piperidinyl, N-acetylpiperidinyl, N-methylpiperidinyl, N-formylpiperazinyl, N-methylsulfonylpiperazinyl, homopiperazinyl, piperazinyl, azetidinyl, oxetanyl, morpholinyl, tetrahydroisoquinolinyl, tetrahydroquinolyl, indolinyl, tetrahydropyranyl, dihydrogen-2H-pyranyl, tetrahydrofuranyl, tetrahydrothiopyranyl, tetrahydrothiopyran-1-oxide, tetrahydrothiopyran-1,1-dioxide, 1H-pyridin-2-one and 2,5-dioxoimidazolidinyl.

In terms of the location and nature of different substituents, the compounds of the present specification may further contain one or more asymmetric centers. The asymmetric carbon atom may has (R) or (S) configuration. A racemic mixture is obtained with one asymmetric center; and a mixture of diastereomers is obtained with multiple asymmetric centers. In some cases, asymmetry is also produced due to hindrance of rotation around a particular bond, for example, when the particular bond is connected with two substituted aromatic rings in the compound. In addition, the substituents may exist in a cis- or trans-isomer form.

The compounds of formula (I) also include all possible stereoisomers thereof, which are single stereoisomers or mixtures of stereoisomers (for example R-isomers or S-isomers, or E-isomers or Z-isomer) in any ratio. Single stereoisomers (e.g., single enantiomers or single diastereomers) of the compounds of the present specification can be obtained by a separation method according to any suitable prior art (for example, chromatography, particularly, chiral chromatography).

Additionally, the compounds may also exist in tautomeric forms. The compounds of the present specification include all possible tautomers of the compounds of formula (I), which are in a form of a single tautomer or any mixture of the tautomers in any ratio.

All such isomers and mixtures thereof are included in the present specification.

Those skilled in the art will appreciate that the NEP inhibitors and the compounds of formula (I) of the present specification may exist in a form of various pharmaceutically acceptable salts. If these compounds have an alkaline center, acid addition salts may be formed; if these compounds have an acidic center, alkaline addition salts may be formed; and if these compounds contain both an acidic center (such as a carboxyl group) and an alkaline center (such as an amino group), an internal salt may be formed.

In the present specification, the acid addition salts include, but are not limited to, hydrochloride, hydrofluoride, hydrobromide, hydroiodide, sulfate, pyrosulfate, phosphate, nitrate, methanesulfonate, ethanesulfonate, 2-hydroxyethanesulfonate, besylate, tosylate, sulfamate, 2-naphthalenesulfonate, formate, acetoacetate, pyruvic acid, laurate, cinnamate, benzoate, acetate, diglycolic acid salt, trifluoroacetate, trimethylacetate, propionate, butyrate, hexanoate, heptanoate, undecanoate, stearate, ascorbate, camphorate, camphor sulfonate, citrate, fumarate, malate, maleate, hydroxymaleate, oxalate, salicylate, succinate, gluconate, quinate, pamoate, glycolate, tartrate, lactate, 2-(4-hydroxybenzoyl)benzoate, cyclopentane propionate, digluconate, 3-hydroxy-2-naphthoate, nicotinate, pamoate, pectate ester, 3-phenylpropionate, picrate, pivalate, itaconate, triflate, lauryl sulfate, p-toluenesulfonate, naphthalene disulfonate, malonate, adipate, alginate, mandelate, glucoheptonate, glycerin phosphate, sulfosalicylic acid salt, hemisulfuric acid or thiocyanate, aspartate, etc.; and the alkaline addition salts can be exemplified as alkali metal salts, alkaline earth metal salts and ammonium salts, etc., which include but are not limited to: sodium salt, lithium salt, potassium salt, ammonium salt (including salts formed from $NH_3$ and organic amine), aluminum salt, magnesium salt, calcium salt, barium salt, iron salt, ferrous salt, manganese salt, manganese salt, zinc salt, $NH_4$ salt, methylamine salt, trimethylamine salt, diethylamine salt, triethylamine salt, propylamine salt, tripropylamine salt, isopropylamine salt, tert-butylamine salt, N,N'-dibenzylethylenediamine salt, dicyclohexylamine salt, 1,6-hexanediamine salt, benzylamine salt, ethanolamine salt, N,N-dimethylethanolamine salt, N,N-diethylethanolamine salt, triethanolamine salt, tromethamine salt, lysine salt, arginine salt, histidine salt, glucosamine salt, N-methylglucamine salt, dimethyl glucosamine salt, ethyl glucosamine salt, N-methylglucamine salt, betaine salt, caffeine salt, chloroprocaine salt, procaine salt, lidocaine salt, pyridinium salt, methylpyridine salt, piperidine salt, morpholine salt, piperazine salt, purine salt, theobromine salt, choline salt and the like.

It will be understood by those skilled in the art that the NEP inhibitors and the compounds of formula (I) of the present specification may also exist in various pharmaceutically acceptable ester forms including, but are not limited to, methyl ester, ethyl ester, propyl ester, propyl ester, butyl ester, isobutyl ester, tert-butyl ester and the like.

In a preferred embodiment, the NEP inhibitor and the pharmaceutically acceptable salts of the compound of formula (I) are independently selected from the group consisting of sodium, potassium or ammonium salts; the NEP inhibitor or the pharmaceutically acceptable esters of the compound of formula (I) are independently selected from the group consisting of methyl ester, ethyl ester or propyl ester.

According to an exemplary embodiment of the present disclosure, the NEP inhibitor may be sacubitril, its stereoisomer or a mixture thereof in any ratio.

In a preferred embodiment, the compound of formula (I) has a chemical structure shown below:

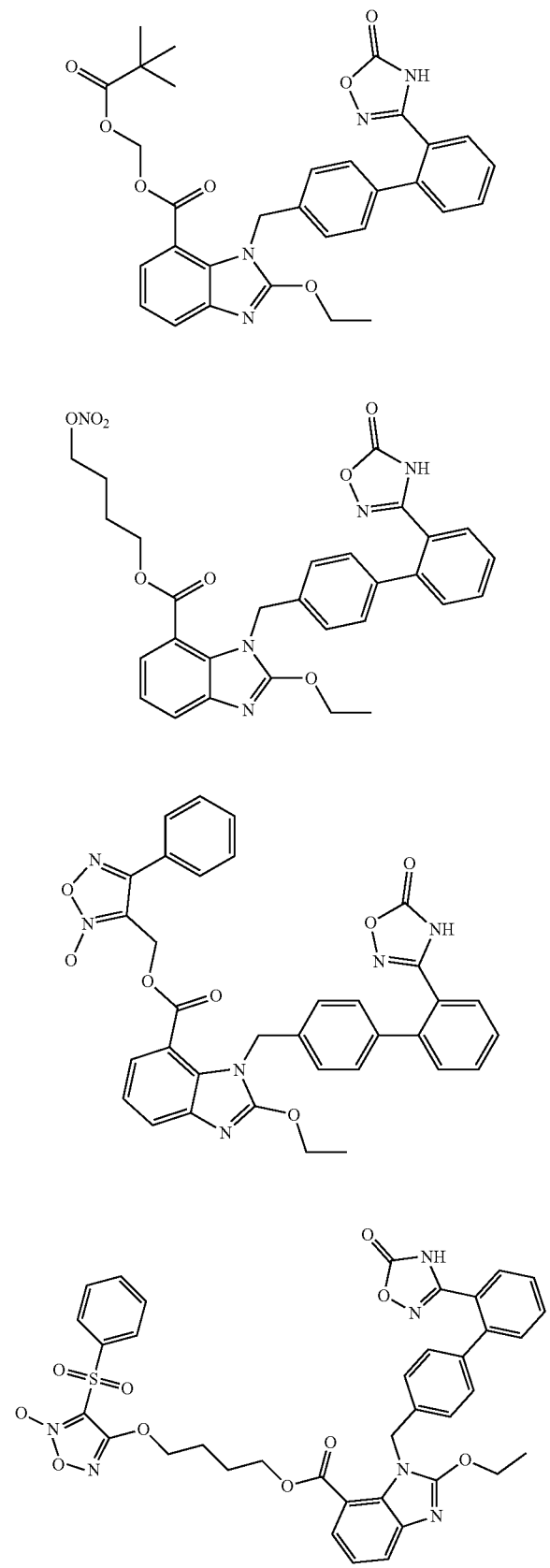

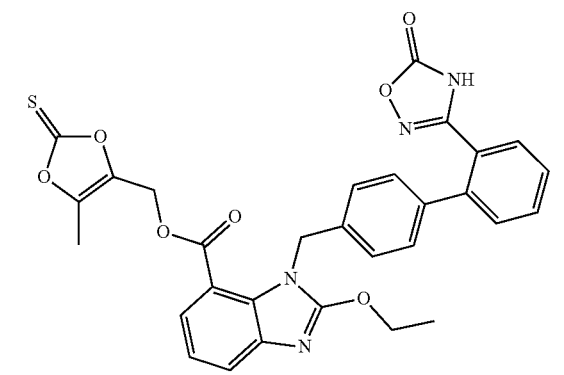
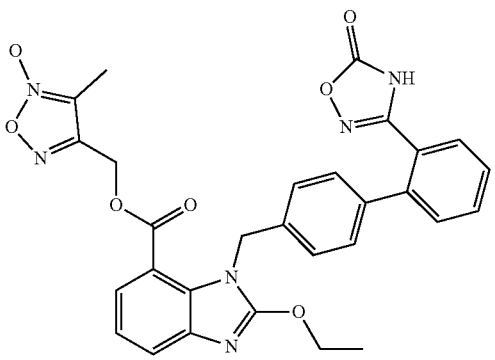
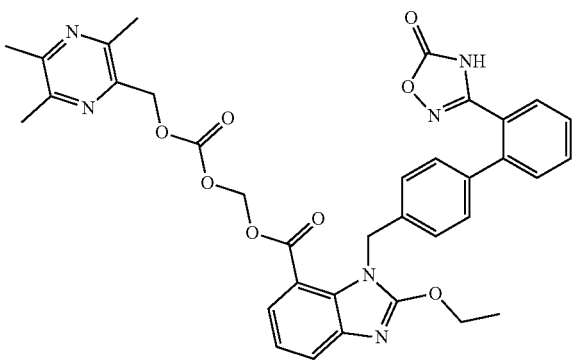
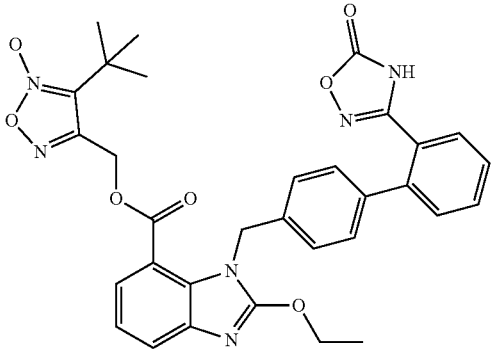
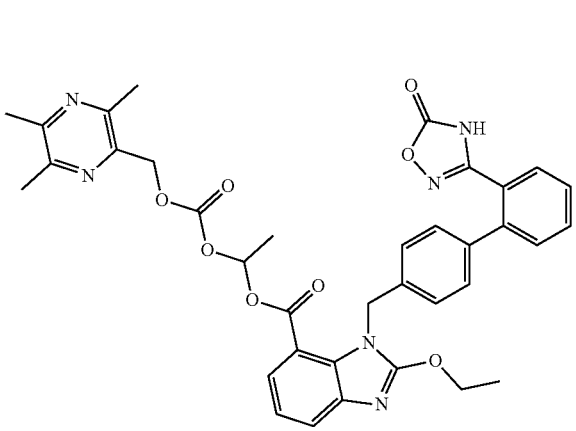
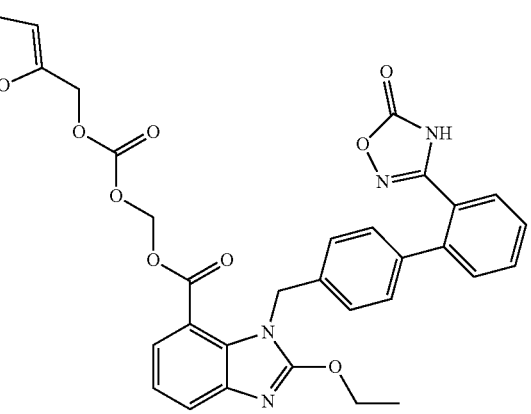
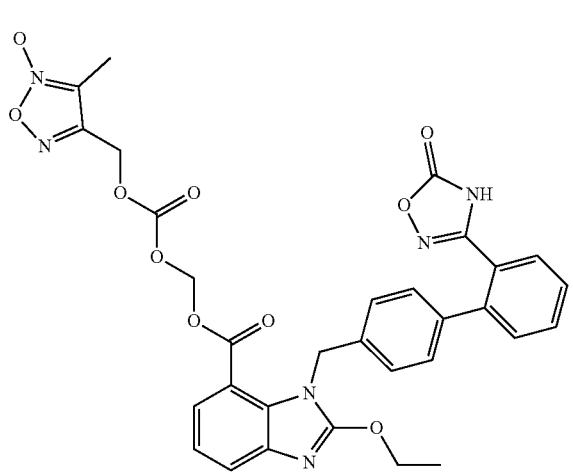
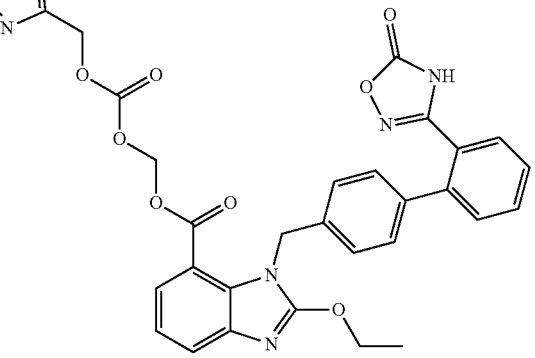

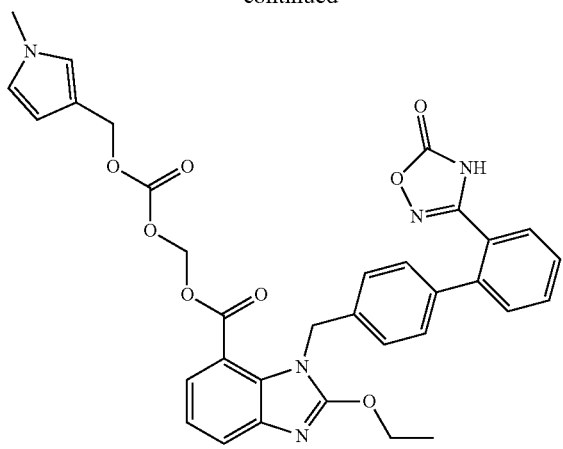

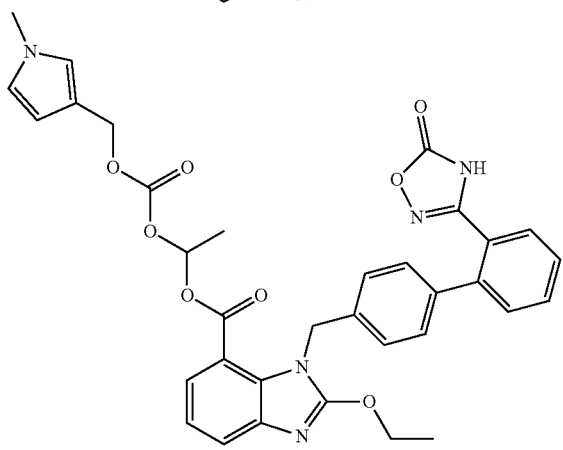

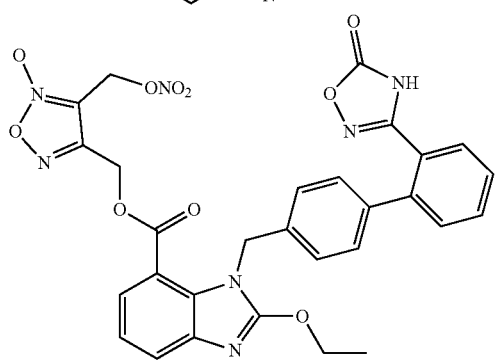

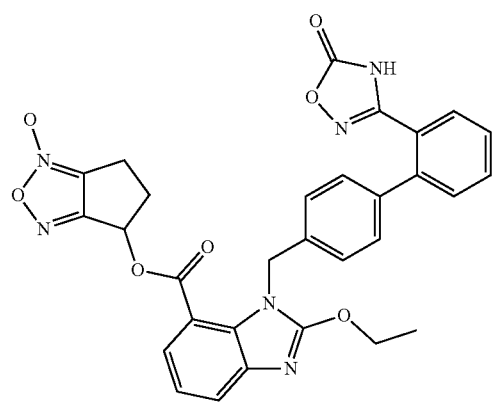

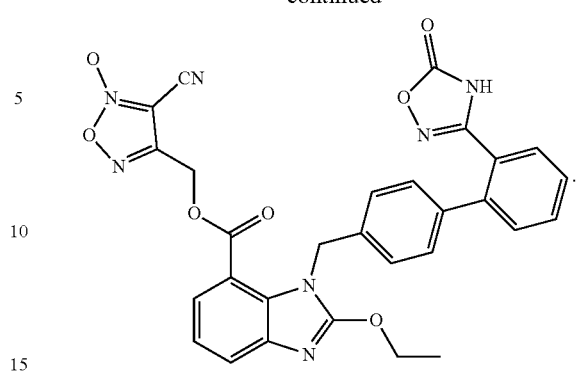

In a preferred embodiment, the pharmaceutically acceptable salt of the compound of formula (I) is potassium salt; and further preferably, the potassium salt of the compound of formula (I) has a chemical structure represented by the following formula (II):

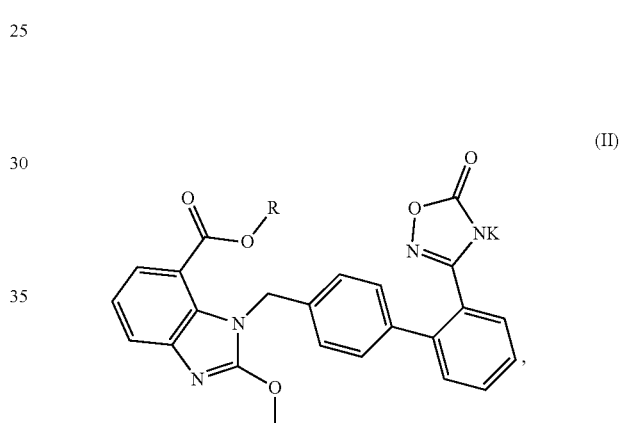

(II)

wherein R is as defined above.

In a further preferred embodiment, the potassium salt of the compound of formula (I) has a chemical structure shown below:

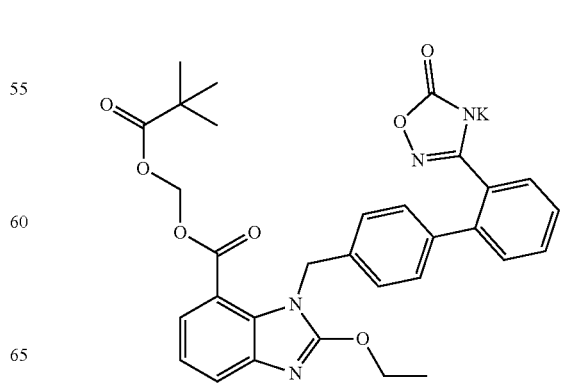

15
-continued
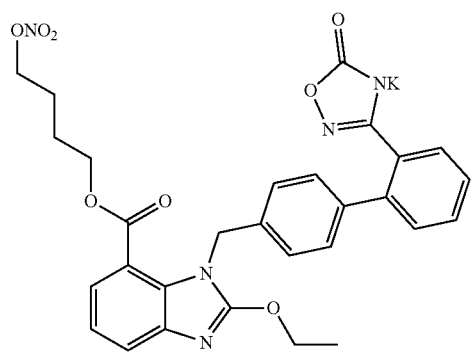
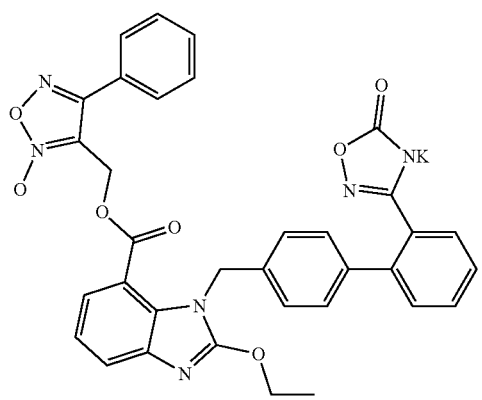
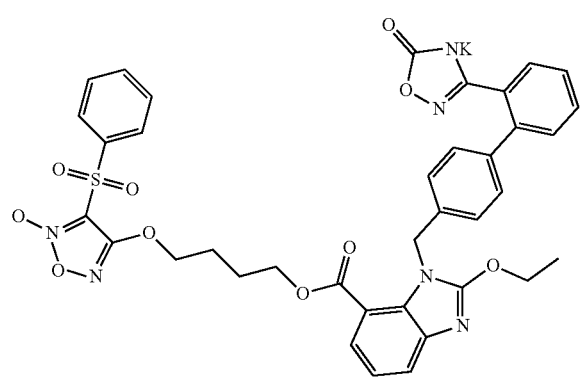
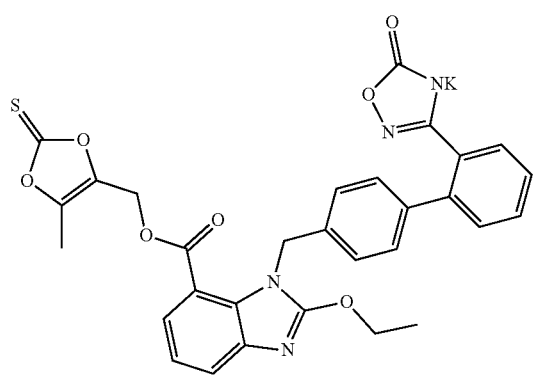
16
-continued
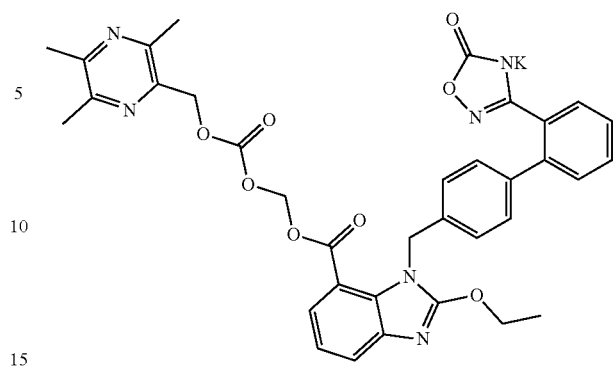
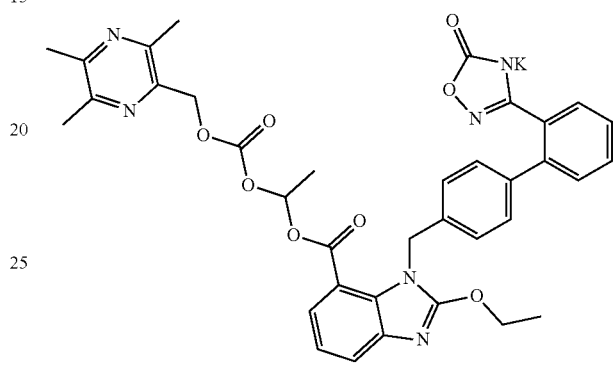
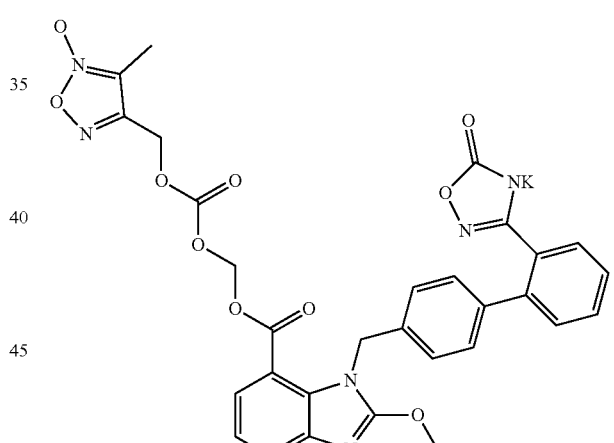
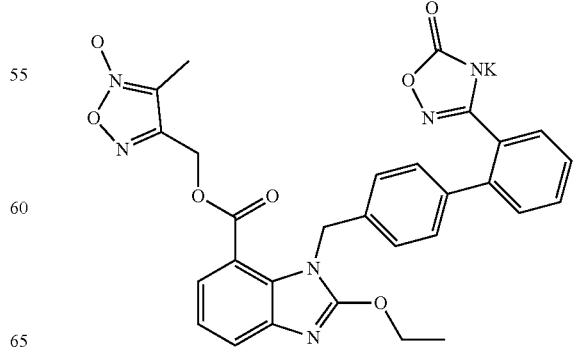

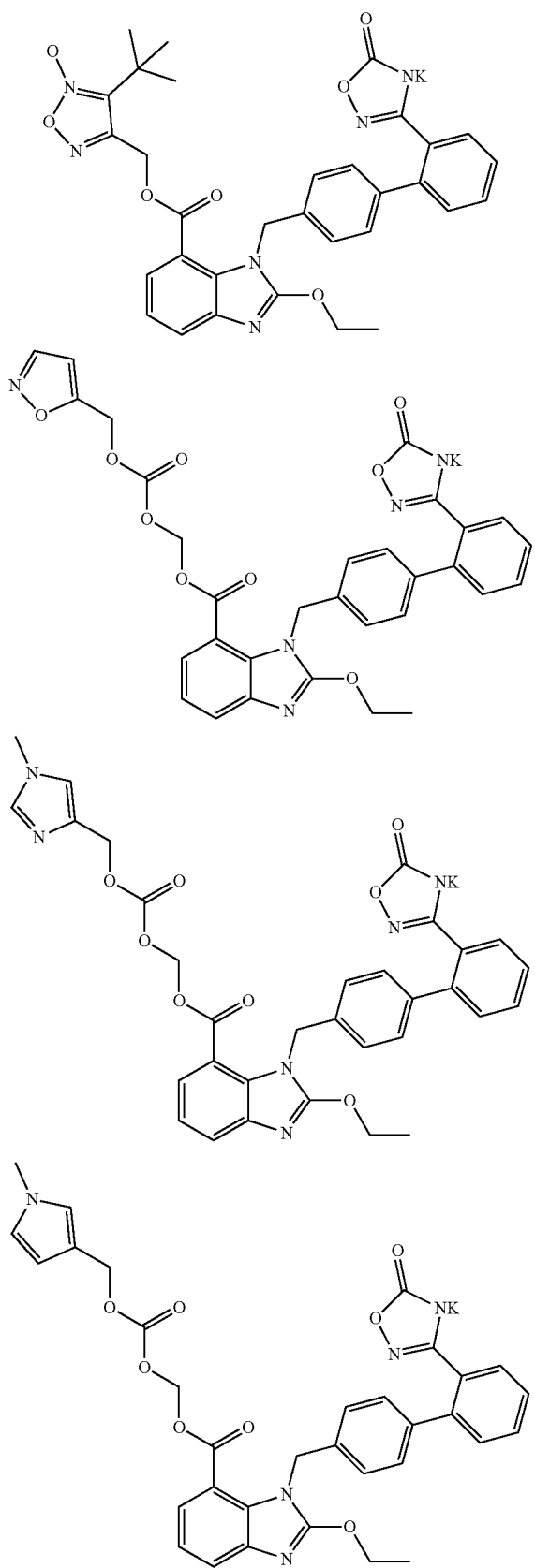
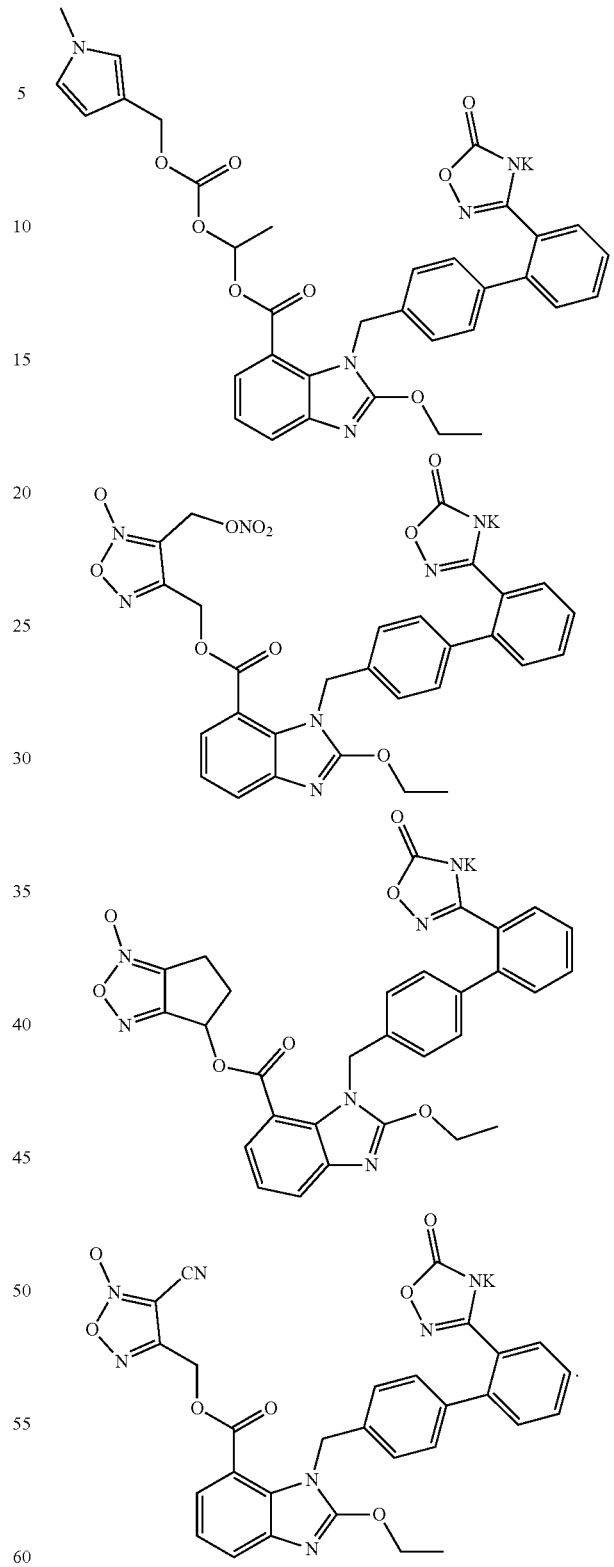
In a preferred embodiment, the (a) is at least one of the following compounds or pharmaceutically acceptable salt or ester thereof:
(S)-(2-biphenyl-4-yl)-1-(1H-tetrazol-5-yl)ethylamino)methylphosphonic acid, (S)-5-(N-(2-(phosphonomethyl-amino)-3-(4-biphenyl)-propionyl)-2-aminoethyl)tetrazole, (±) N-(1-oxo-2-indolyl-3-phenylpropionyl)glycine, N-((2S)-2-(4-biphenylmethyl)-4-carboxy-5-phenoxypentanoyl)glycine, N-(α-rhamnopyranosylphosphonamide)-L-leucine-L-tryptophan, N—[N-[(L)-1-carboxy-2-phenylethyl]-L-phenylalanyl]-(R)-alanine, N—[N-[((1S)-carboxy-2-phenyl)ethyl]-(S)-phenylalanyl]-3-alanine, N—(S)-[3-mercapto-2-(2-methylphenyl)propanoyl]-(S)-2-methoxy-(R)-alanine, 3-[1,1'-biphenyl]-4-yl-N-[diphenoxyphosphinyl)-methyl]-L-alanyl-3-alanine, N-(1-(N-hydroxycarbamoyl-methyl)-1-cyclopentanecarbonyl)-L-phenylalanine, N-[2-mercaptomethyl-3-phenyl-propionyl]-3-aminobenzoic acid, 4-[[2-(mercaptomethyl)-1-oxo-3-phenylpropyl]amino]benzoic acid, N-[2-acetylthiomethyl-3-phenyl-propionyl]-3-aminobenzoic acid, N-[2-mercaptomethyl-3-(2-methylphenyl)-propionyl]-methionine, N-(3-phenyl-2-(mercaptomethyl)-propionyl)-(S)-4-(methylmercapto)-methionine, N-[1-(2-carboxy-4-phenylbutyl)-cyclopentanecarbonyl]-(S)-isoserine, N-[2(S)-nonylmethyl-3-(2-methylphenyl)propanoyl]-(S)-isoserine, N-(1-(3-(N-tert-butoxycarbonyl-(S)-prolylamino)-2(S)-tert-butoxy-carbonylpropyl)cyclopent anecarbonyl)-O-benzyl-(S)-serine, 3(S)-[2-(acetylthiomethyl)-3-phenyl-propionyl]amino-ε-caprolactam, N-[1-(acetylthiomethyl)-cyclopentylcarbonyl]-(S)-methionine, N-[2-acetylthiomethyl-3-(2-methyl-phenyl)propanoyl]-methionine, N-[2(S)-mercaptomethyl-3-(2-methylphenyl)-propionyl] methionine, N-[2-(mercaptomethyl)-1-oxo-3-phenylpropyl]-β-alanine, 7-[[2-(mercaptomethyl)-1-oxo-3-phenylpropyl]amino]-heptanoic acid, N—N-[1 (S)-carboxy-3-phenylpropyl]-(S)-phenylalanyl]-(S)-isoserine, N-[1-[[1 (S)-carbonyl-3-phenylpropyl]amino-cyclopentylcarbonyl]-(S)-isoserine, N-[1-[[1 (S)-benzyloxycarbonyl-3-phenylpropyl]amino]-cyclopentylcarbonyl]-(S)-isoserine, N—[N-[(L)-[1-[(2,2-dimethyl-1,3-dioxolan-4-yl)-methoxy] carbonyl]-2-phenylethyl]-L-phenylalanyl]-(R)-alanine, N-(2-carboxy-4-thienyl)-3-mercapto-2-benzylpropanamide, 2-(2-mercaptomethyl-3-phenylpropionylamino)thiazole-4-ylcarboxylic acid, (L)-(1-((2,2-dimethyl-1,3-dioxolan-4-yl)-methoxy)carbonyl)-2-phenylethyl)-L-phenylalanyl-β-alanine, cis-4-[[[1-[2-carboxy-3-(2-methoxyethoxy)propyl]-cyclopentyl]carbonyl]amino]-cyclohexanecarboxylic acid, 3-(1-[6-endo-hydroxymethylbicyclo[2,2,1]heptane-2-exo-carbamoyl]cyclopentyl)-2-(2-meth oxyethyl)propane acid, 3-[1-(cis-4-carboxycarbonyl-cis-3-butylcyclohexyl-r-1-carbamoyl)cyclopentyl]-2S-(2-methoxyethoxy-methyl)propionic acid, (S)-cis-4-[1-[2-(5-indanyloxy-carbonyl)-3-(2-methoxyethoxy)propyl]-1-cyclopentanoylamino] 1-cyclohexanecarboxylic acid, 1,1'-[dithiobis-[2(S)-(2-methylbenzyl)-1-oxo-3,1-propylene]]-bis-(S)-isoserine, 1,1'-[dithiobis-[2(S)-(2-methylbenzyl)-1-oxo-3,1-propylene]]-bis-(S)-methylthioamide acid, 4-(((2S,4R)-1-([1,1'-biphenyl]-4-yl)-5-ethoxy-4-methyl-5-oxopentan-2-yl)amino)-4-oxobutanoic acid, N-(3-carboxy-1-oxopropyl)-(4S)-p-phenylphenylmethyl)-4-amino-2R-methylbutyric acid.

In a further preferred embodiment, the (a) is at least one of the following compounds:

N-[1-(acetylthiomethyl)-cyclopentylcarbonyl]-(S)-methionine ethyl ester,

N-[2-acetylthiomethyl-3-(2-methyl-phenyl)propanoyl]-methionine ethyl ester,

N-(1-(3-(N-tert-butoxycarbonyl-(S)-prolylamino)-2(S)-tert-butoxy-carbonylpropyl)cyclopent anecarbonyl)-O-benzyl-(S)-serine methyl ester, 3(S)-[2-(acetylthiomethyl)-3-phenyl-propionyl]amino-ε-caprolactam, 4-(((2S,4R)-1-([1,1'-biphenyl]-4-yl)-5-ethoxy-4-methyl-5-oxopentan-2-yl) amino)-4-oxobutyric acid (AHU 377 or sacubitril), N-(3-carboxy-1-oxopropyl)-(4S)-p-phenylphenylmethyl)-4-amino-2R-methylbutyric acid, N-(3-carboxy-1-oxopropyl)-(4S)-p-phenylphenylmethyl)-4-amino-2R-methylbutyrate sodium, N-(3-carboxy-1-oxopropyl)-(4S)-p-phenylphenylmethyl)-4-amino-2R-methylbutyrate potassium, ethyl 4-(((2S,4R)-1-([1,1'-biphenyl]-4-yl)-5-ethoxy-4-methyl-5-oxopentan-2-yl) amino)-4-oxobutanoate (AHU 377 ethyl ester or sacubitril ethyl ester), sodium 4-(((2S,4R)-1-([1,1'-biphenyl]-4-yl)-5-ethoxy-4-methyl-5-oxopentan-2-yl) amino)-4-oxobutyrate (AHU 377 sodium salt or sacubitril sodium salt), potassium 4-(((2S,4R)-1-([1,1'-biphenyl]-4-yl)-5-ethoxy-4-methyl-5-oxopentan-2-yl) amino)-4-oxobutanoate (AHU 377 potassium salt or sacubitril potassium salt), ammonium 4-(((2S,4R)-1-([1,1'-biphenyl]-4-yl)-5-ethoxy-4-methyl-5-oxopentan-2-yl) amino)-4-oxobutanoate (AHU 377 ammonium salt or sarbuteramine ammonium salt).

In a preferred embodiment, the (a) is AHU 377, AHU 377 ethyl ester, AHU 377 sodium, AHU 377 potassium, N-(3-carboxy-1-oxopropyl)-(4S)-p-phenylbenzene methyl)-4-amino-2R-methylbutyric acid, sodium N-(3-carboxy-1-oxopropyl)-(4S)-p-phenylphenylmethyl)-4-amino-2R-methylbutyrate, potassium N-(3-carboxy-1-oxopropyl)-(4S)-p-phenylphenylmethyl)-4-amino-2R-methylbutyrate or ammonium 4-(((2S,4R)-1-([1,1'-biphenyl]-4-yl)-5-ethoxy-4-methyl-5-oxopentan-2-yl)amino)-4-oxobutyrate;

In a preferred embodiment, the (b) is the following compound 1K:

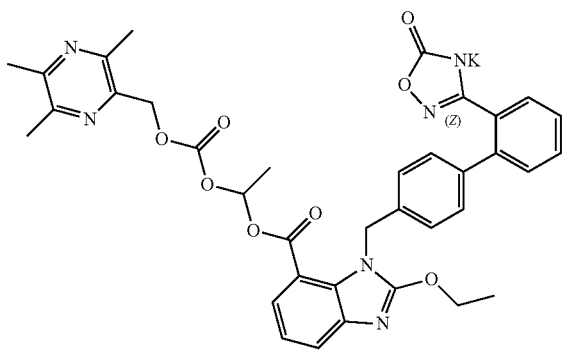

Further preferably, the compound 1K may be amorphous, any one of the crystalline forms I, II, III, IV, or a mixture thereof in any ratio; and further preferably, the compound 1K may be the crystalline form I or the crystalline form II of the compound 1K or a mixture thereof in any ratio.

In the present specification, a mass ratio of the (a) to the (b) is (0.5-10):1, for example, 10:1, 9:1, 8:1, 7:1, 6:1, 5:1, 4:1, 3:1, 2:1, 1:1, 0.5:1; preferably (0.5-5):1, and more preferably (0.5-3):1, for example: 3:1, 2.5:1, 2:1, 1.9:1, 1.8:1, 1.7:1, 1.6:1, 1.5:1, 1.45:1, 1.4:1, 1.35:1, 1.3:1, 1.25:1, 1.2:1, 1.15:1, 1.1:1, 1.05:1, 1:1, 0.95:1, 0.9:1, 0.85:1, 0.8:1, 0.75:1, 0.7:1, 0.65:1, 0.6:1, 0.55:1, or 0.5:1.

In the present specification, cardiovascular diseases include, but are not limited to, hypertension, heart failure, coronary heart disease, rheumatic heart disease, congenital heart disease, left ventricular dysfunction, endothelial dysfunction, diastolic dysfunction, hypertrophic cardiomyopathy, diabetic cardiomyopathy, supraventricular and ventricular arrhythmia, atrial fibrillation, cardiac fibrosis, atrial flutter, harmful vascular remodeling, myocardial infarction and its sequelae, atherosclerosis, angina pectoris, primary and secondary pulmonary hypertension and renal vascular hypertension, etc.

The pharmaceutical compositions or pharmaceutical kits of the present specification can be prepared by methods well known in the art. The pharmaceutical composition or the pharmaceutical composition in the pharmaceutical kit of the present specification may be formulated into various dosage forms suitable for oral, inhalation, rectal, topical, parenteral, etc. administration, including, but not limited to, powders suitable for oral administration, tablets (including various coated tablets, sustained release or controlled release tablets), lozenges, capsules (including soft and hard capsules), granules, pills, dispersible powders, aqueous or oily suspensions, aqueous or oily solutions, emulsions, elixirs, syrups, etc.; inhalable powders or liquid aerosols; suppository for rectal, etc.; creams, ointments, gels, water-based or oily solutions, aqueous or oily suspensions etc.; suitable for topical; sterile aqueous or oily injection or lyophilized powder suitable for parenteral administration via intravenous, subcutaneous or intramuscular injection. The pharmaceutical composition of the present specification can be administered as an integrated pharmaceutical kit or as separate components at different doses or at different time intervals.

Pharmaceutically acceptable carriers include, but are not limited to, fillers (or diluents), binders, disintegrants, lubricants, wetting agents, auxiliary lipids, glidants, sweeteners, flavoring agents, solvents, cosolvent, suspending agents, isotonic agents, buffers, preservatives, antioxidants, colorants, foaming agents and the like. Those skilled in the art can select the above pharmaceutically acceptable carrier according to actual demands. For example, fillers (diluents) which may be used include, but are not limited to, lactose, sucrose, microcrystalline cellulose, starch, mannitol, mannitol-starch, etc.; binders which may be used include, but are not limited to, microcrystalline cellulose, povidone, tragacanth, glucose solution, gum arabic, gelatin solution, sucrose, starch paste, etc.; disintegrators which may be used include, but are not limited to, croscarmellose sodium, low-substituted hydroxypropyl cellulose, crospovidone, sodium starch glycolate, alginic acid, dry starch, bentonite, methyl cellulose, agar, carboxymethyl cellulose, etc.; lubricants which may be used include, but are not limited to, talc, magnesium or calcium stearate, lycopodium, etc.; humectants which may be used include, but are not limited to, propylene glycol monostearate, sorbitan monooleate, diethylene glycol monolaurate and polyoxyethylene lauryl ether; auxiliary lipids which may be used include, but are not limited to, phosphatidylethanolamine, phosphatidylcholine, cholesterol, etc.; glidants which may be used include, but are not limited to, colloidal silica, and the like; sweeteners which may be used include, but are not limited to, sucrose, lactose, mannitol, artificial sweeteners (such as sodium cyclamate and sugar), etc.; and flavoring agents which may be used include, but are not limited to, peppermint and methyl salicylate and the like.

The dosage and unit dose of the active ingredient of the pharmaceutical composition or pharmaceutical kit of the present specification can be determined by methods well known in the art. For example, the dosage for oral administration is in an amount of from 1 to 200 mg, preferably from 5 to 150 mg, and more preferably from 5 to 100 mg per day, based on the content of the compound represented by the formula (I).

The pharmaceutical composition or the pharmaceutical kit of the present specification may further contain another active ingredient such as a diuretic, a calcium ion antagonist and the like.

In comparison with the prior art, the technical solution of the present specification has advantages and beneficial effects in that: the combination application of the NEP inhibitor and the angiotensin II receptor antagonist represented by the formula (I) of the present specification contributes to unexpected synergistic effect, bringing more stable or long-lasting effect in lowering blood pressure and/or lowering the heart rate, as well as improvement of heart function. Therefore, the pharmaceutical combination of the present specification has a good curative effect in treating acute and chronic heart failure, and can be applied at a lower dose or a lower frequency for desired effect, with decreased advise effect compare to single drugs.

DETAILED DESCRIPTION

The invention will be further elucidated below in conjunction with specific embodiments. It should be understood that the examples are intended to illustrate the invention but not to limit the scope of the invention. In addition, it should be understood that various modifications and changes may be made to the present invention by those skilled in the art after the disclosure of the present invention, therefore technical solutions with these modifications and changes are also within the scope of the present invention.

Example 1. Preparation of the Compound 1K

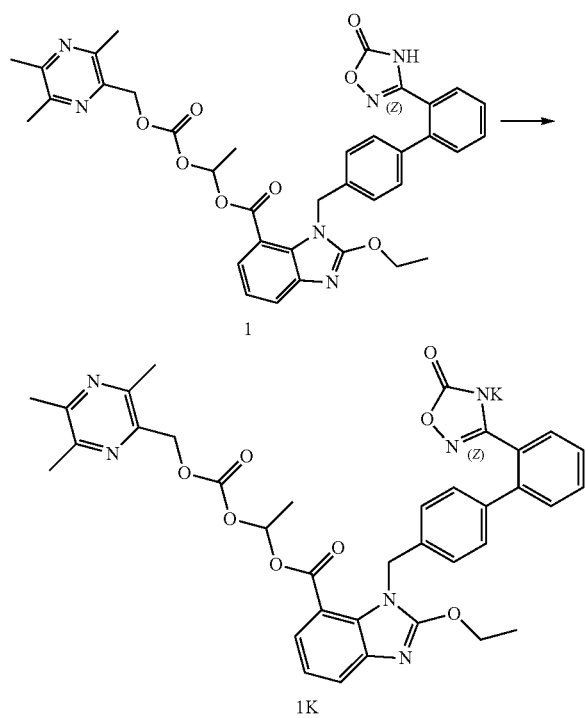

Compound 1 (1.0 g) was dissolved in dichloromethane (5 ml) to obtain a mixture, and the mixture was stirred at room temperature to form a solution, which was then added with potassium phthalimide (0.27 g), kept for 4 hours at room temperature, and cooled to −50° C., followed by filtration and drying via rotary evaporation to obtain a solid of the compound 1K (amorphous form).

Melting point: 135-145° C. MS/HRMS m/z: 717 [M+H]$^+$; 677 [M−K]$^-$. $^1$H-NMR (400 MHz, DMSO-d$_6$) δ: 1.44 (t, 3H), 1.46 (t, 3H), 2.38 (s, 3H), 2.41 (s, 3H), 2.44 (s, 3H), 4.64 (q, 2H), 5.29 (d, 1H), 5.32 (d, 1H), 5.52 (d, 1H), 5.56 (d, 1H), 6.86 (q, 1H), 6.90 (d, 2H), 7.18 (m, 2H), 7.22 (d, 2H), 7.33 (m, 1H), 7.36 (m, 1H), 7.46 (d, 1H), 7.52 (dd, 1H), 7.75 (d, 1H).

Figure 1:
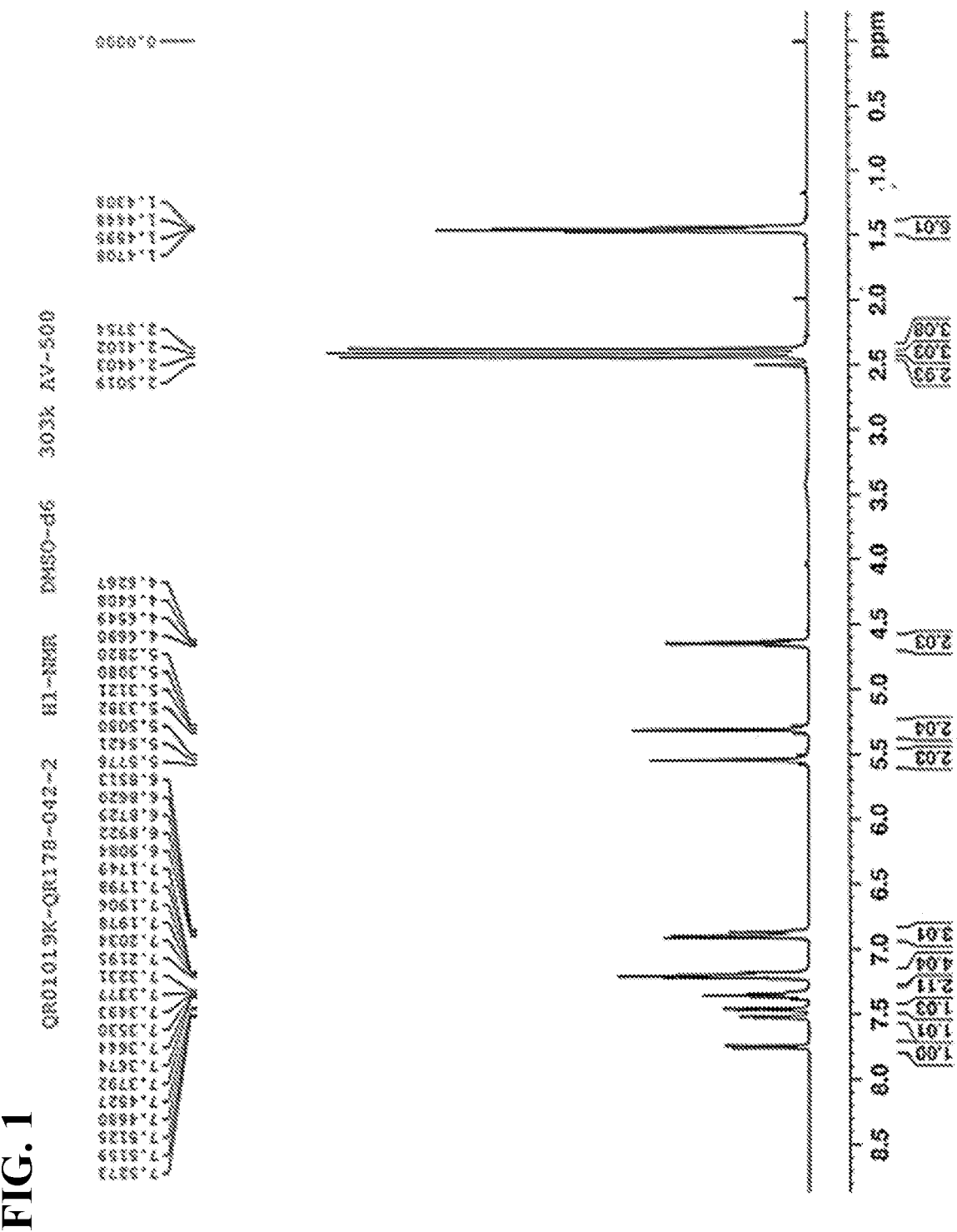
FIG. 1 is a $^1$H-NMR spectrum of the compound 1K.
Figure 2:
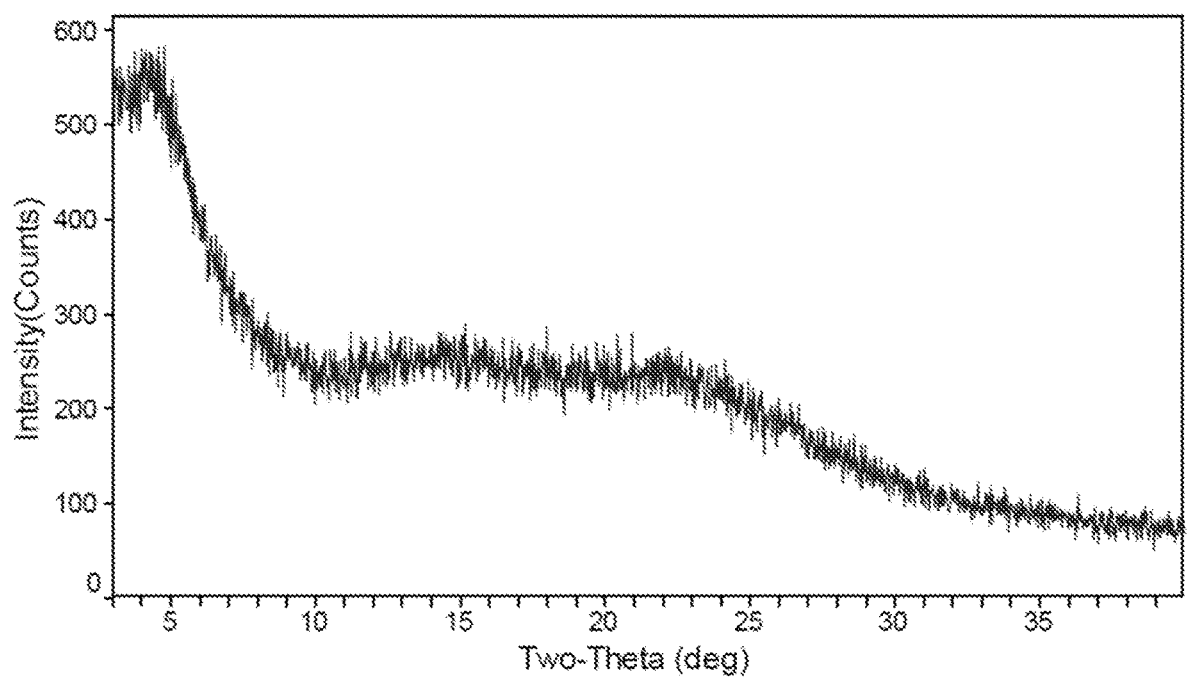
FIG. 2 is an X-ray powder diffraction pattern of the amorphous form of the compound 1K.

The $^1$H-NMR spectrum and the X-ray powder diffraction pattern are shown in FIG. 1 and FIG. 2, respectively.

Figure 3:
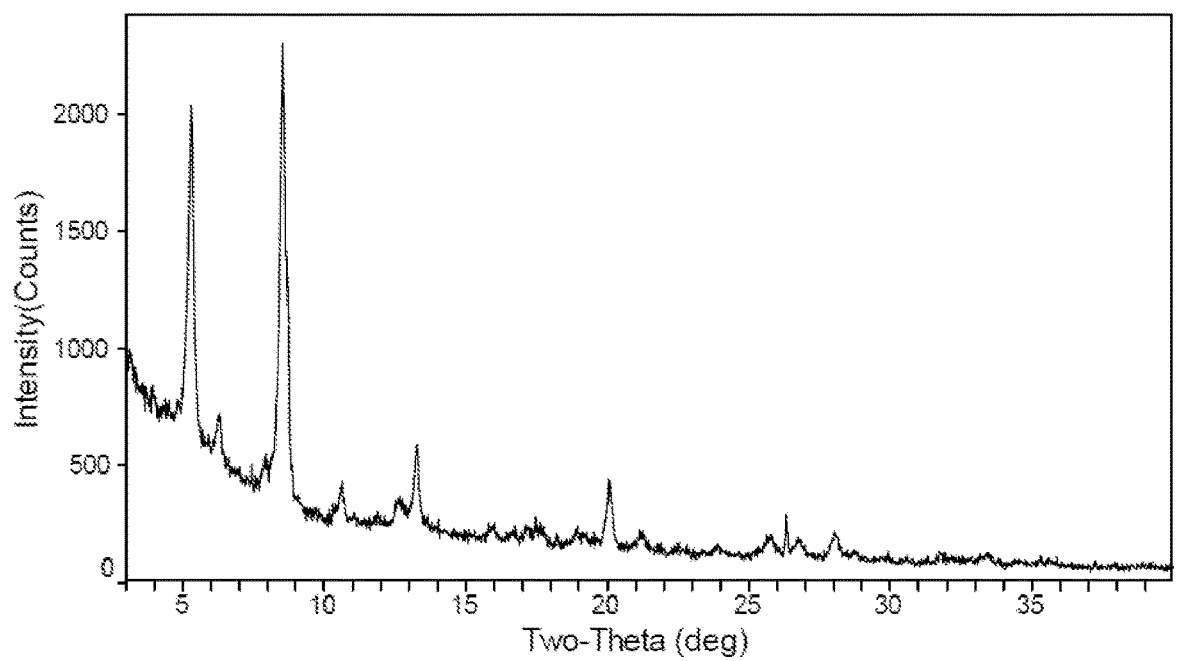
FIG. 3 is an X-ray powder diffraction pattern of the crystalline form I.

Example 2. Preparation of Crystalline Form I of Compound 1K 15 mg compound 1K was added with a mixed solution of 0.2 ml ethanol/isopropyl ether (1:5 v/v) to obtain a suspension, which was stirred at room temperature for 1 day, filtered, and dried to give a crystalline form I. The XRD detection pattern is shown in FIG. 3; DSC: 184° C.

Figure 4:
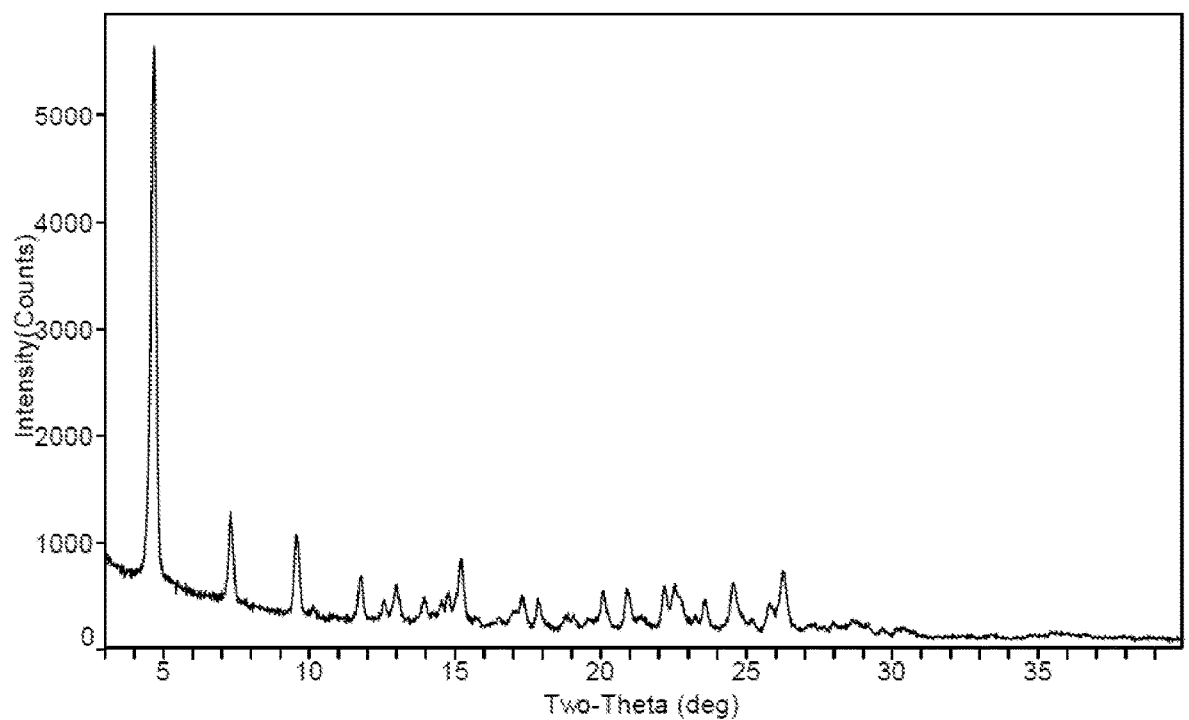
FIG. 4 is an X-ray powder diffraction pattern of the crystalline form II.

Example 3. Preparation of Crystalline Form II of the the Compound 1K 1.1 g of the compound 1K was added with 10 ml ethyl acetate to obtain a clear solution, which was stirred at room temperature for 3 hours, filtered and dried to obtain 0.88 g product. The X-ray powder diffraction pattern of the obtained crystalline form II is shown in FIG. 4; DSC: 145.4° C.

Figure 5:
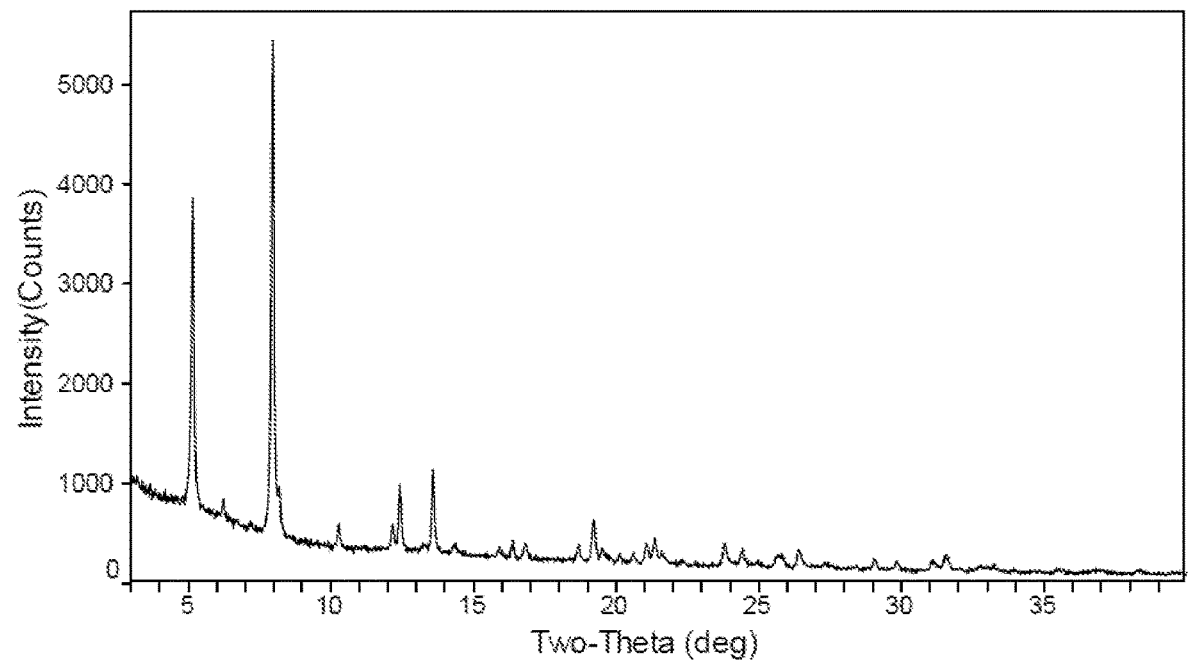
FIG. 5 is an X-ray powder diffraction pattern of the crystalline form III.

Example 4. Preparation of Crystalline Form III of the Compound 1K 100 mg compound 1K was added with 1.0 ml tetrahydrofuran to obtain a suspension, which was stirred at room temperature for 1 day, filtered, and dried. The X-ray powder diffraction pattern of the obtained crystalline form III is shown in FIG. 5; DSC: 187.3° C.

Figure 6:
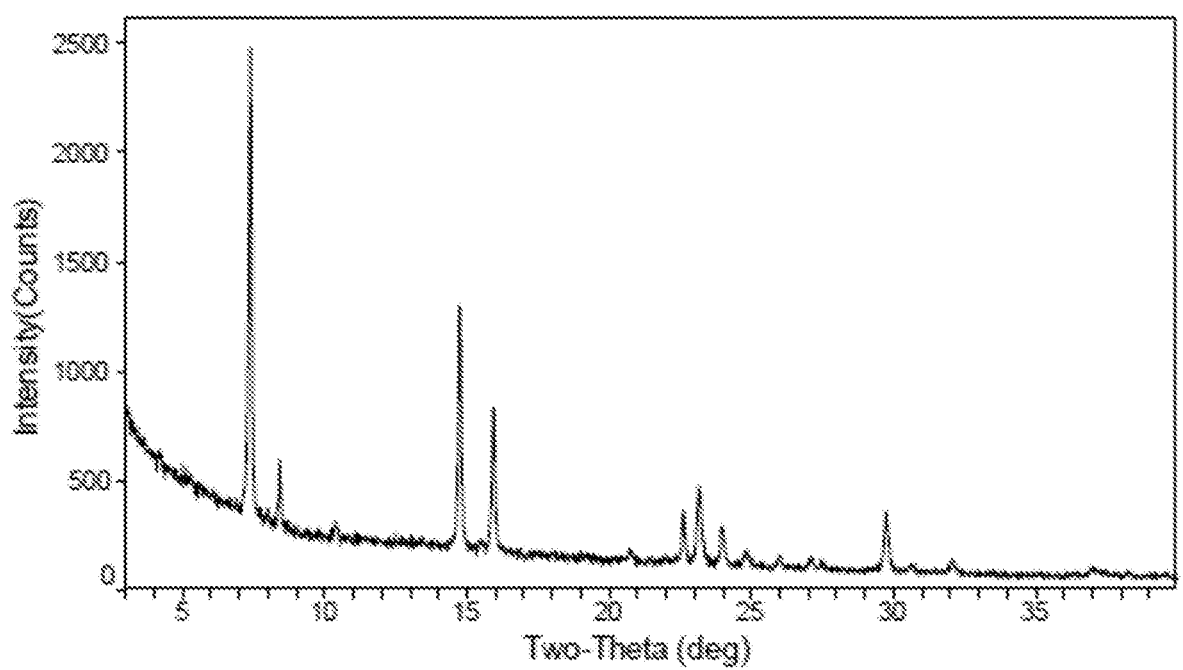
FIG. 6 is an X-ray powder diffraction pattern of the crystalline form IV.

Example 5. Preparation of Crystalline Form IV of the Compound 1K 50 mg compound 1K was dissolved in 1.0 ml n-butanol to obtain a clear solution, added with 5.0 ml n-heptane under stirring to precipitate a solid and filtered. The X-ray powder diffraction pattern of the obtained crystalline form IV is shown in FIG. 6; DSC melting point: 144.7° C.

Example 6. Preparation of a Mixture of the Crystalline Form I and the Crystalline Form II 100 mg crystalline form II was added with 2.5 ml isopropyl acetate to obtain a suspension, which was stirred in a water bath at 80° C. for 8 hours, filtered, and dried. It is determined by XRD and HPLC that the crude product contains about 95% of the crystalline form I and about 5% of the crystalline form II.

Example 7. Antihypertensive Efficacy Test of the Compound 1K in Spontaneously Hypertensive Rats 12-week-old spontaneously hypertensive rats (hereinafter referred to as SHR, purchased from Beijing Weitong Lihua Experimental Animal Technology Co., Ltd.) were anesthetized with 2.5% sodium pentobarbital for intraperitoneal injection. After that, the blood pressure sensing catheter of hypertension implant was inserted into their abdominal aorta, while the implant was fixed to the abdominal wall, and then postoperative daily care was performed after suturing. Rats with systolic blood pressure exceeding 160 mm Hg were divided into 3 groups (control group, compound 1 group and compound 1K group), wherein each group has 8 rats. The control group was administrated 0.5% sodium carboxymethyl cellulose (hereinafter referred to as CMC-Na); the compound 1 group and the compound 1K group were respectively administered the compound 1 and the compound 1K, both of which were dissolved by 0.5% CMC-Na, by intragastric administration, at a dose of 1 mg/kg (calculated by the effective dose of valsartan) and a volume calculated by 4 mL/kg. The systolic blood pressure and heart rate of SHR were compared before and after administration (the systolic blood pressure and heart rate of SHR before administration as reference value), which were detected three times at each time point with the average value recorded. The results are shown in Tables 1 and 2 below.

TABLE 1

Systolic blood pressure change at each time point before and after oral administration of the compound 1 and the compound 1K (average (mmHg) ± standard error)

| Group | Before administration | 1 hour after administration | 3 hours after administration | 5 hours after administration |
|---|---|---|---|---|
| Control group | 0.0 ± 0.0 | 5.4 ± 7.1 | −3.5 ± 4.6 | 4.5 ± 4.0 |
| Compound 1 | 0.0 ± 0.0 | −4.9 ± 4.8 | −22.0 ± 3.6* | −30.5 ± 3.5* |
| Compound 1K | 0.0 ± 0.0 | −7.0 ± 3.4 | −34.3 ± 1.9* | −46.5 ± 2.5* |

| Group | 7 hours after administration | 10 hours after administration | 24 hours after administration |
|---|---|---|---|
| Control group | 4.1 ± 3.2 | −2.9 ± 2.3 | −2.7 ± 6.4 |
| Compound 1 | −38.8 ± 2.3* | −33.0 ± 1.7* | −10.2 ± 2.1 |
| Compound 1K | −49.4 ± 4.1* | −45.3 ± 3.3* | −25.9 ± 3.4* |

*P < 0.01 (relative to the control group).

It can be seen from the results in Table 1 that after 3 hours of administration, the systolic blood pressure of the compound 1K or the compound 1 group is significantly decreased compared with the control group, and the drug efficacy peaks 5-7 hours after administration, and the compound 1K group is more potent with longer-lasting antihypertensive effect, compared with the compound 1 group.

TABLE 2

Heart rates change before and after oral administration of the compound 1 and compound 1K (average (times/minute) ± standard error)

| Group | Before administration | 1 hour after administration | 3 hours after administration | 5 hours after administration |
|---|---|---|---|---|
| Control group | 0.0 ± 0.0 | 0.14 ± 2.9 | 6.4 ± 2.8 | −0.3 ± 2.7 |
| Compound 1 | 0.0 ± 0.0 | −3.4 ± 2.6 | −2.33 ± 2.6* | −6.5 ± 2.8* |
| Compound 1K | 0.0 ± 0.0 | −3.6 ± 2.4 | −5.0 ± 2.5* | −10.1 ± 3.0* |

| Group | 7 hours after administration | 10 hours after administration | 24 hours after administration |
|---|---|---|---|
| Control group | −0.1 ± 2.9 | −2.5 ± 2.5 | 4.3 ± 2.8 |
| Compound 1 | −6.2 ± 3.0* | −12.3 ± 2.8* | −6.7 ± 2.6* |
| Compound 1K | −17.5 ± 3.0* | −25.4 ± 2.4* | −28.6 ± 8* |

*P < 0.05 (relative to the one-way ANOVA of the control group).

It can be seen from the results in Table 2 that the compound 1K has more potent with longer-lasting effect of lowering heart rate compared with the compound 1 group.

Example 8. Preparation of Ammonium 4-(((2S,4R)-1-([1,1'-biphenyl]-4-yl)-5-ethoxy-4-methyl-5-oxo-pentane-2-yl)amino)-4-oxobutanoate (AHU 377 Ammonium Salt or Sacubitril Ammonium Salt)

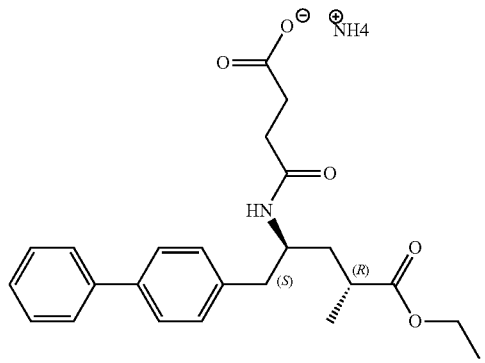

Sacubitril was added to acetone, stirred at room temperature, cooled to 0-10° C., added dropwise with a slight excess of concentrated ammonia water, stirred for another 4 hours after completion of addition, and then filtered, washed with acetone, vacuum-dried to give the target compound with purity of more than 99.5%, MS: m/z=412.3 (M+H)$^+$.

Example 9. Antihypertensive Efficacy Test of Pharmaceutical Compositions in Spontaneously Hypertensive Rats 18-week-old SHRs (purchased from Beijing Weitong Lihua Experimental Animal Technology Co., Ltd.) were anesthetized with 2.5% sodium pentobarbital for intraperitoneal injection. After that, the blood pressure sensing catheter of hypertension implant was inserted into their abdominal aorta, while the implant was fixed to the abdominal wall, and then postoperative daily care was performed after suturing. Rats with systolic blood pressure exceeding 160 mm Hg were divided into 9 groups, wherein each group has 6 rats. A group of WKY rats (provided by Beijing Weitong Lihua Co., Ltd.) was set as a normal control group, which were administered intragastrically once a day at a volume calculated by 4 mL/kg for a total of 4 weeks. Each group were administered as follows:

The normal control group were not administered;
The blank control group were administered 0.5% CMC-Na;
The Compound 1K group were administered the Compound 1K dissolved in 0.5% CMC-Na, at a dose of 1 mg (azilstan effective dose)/kg;

The valsartan group were administered valsartan dissolved in 0.5% CMC-Na, at a dose of 30 mg/kg;

The Azilsartan kaMedoxoMil were administered Azilsartan kaMedoxoMil dissolved in 0.5% CMC-Na, at a dose of 1 mg (azilsartan effective dose)/kg;

The AHU 377K group were administered AHU 377 K, dissolved in 0.5% CMC-Na, at a dose of 30 mg/kg;

The AHU377 ammonium salt group were administered AHU377 ammonium salt, dissolved in 0.5% CMC-Na, at a dose of 30 mg/kg;

The LCZ696 group were administered LCZ696, dissolved in 0.5% CMC-Na, at a dose of 60 mg/kg;

The valsartan+AHU 377K group were administered both valsartan and AHU 377K, dissolved in 0.5% CMC-Na, respectively at a dose of 30 mg (valsartan)/kg and 30 mg (AHU 377K)/kg;

The Azilsartan kaMedoxoMil+AHU 377K group were administered both Azilsartan kaMedoxoMil and AHU 377K, dissolved in 0.5% CMC-Na, respectively at a dose of 1 mg (azilsartan effective dose)/kg and 30 mg (AHU 377K)/kg;

The Compound 1K+AHU 377K group were administered both the compound 1K and AHU 377K, dissolved in 0.5% CMC-Na, respectively at a dose of 1 mg (azilstan effective dose)/kg and 30 mg (AHU 377K)/kg.

The Compound 1K+AHU377 ammonium salt group were administered both the compound 1K and AHU377 ammonium salt, dissolved in 0.5% CMC-Na, at a dose of 1 mg (azilstan effective dose)/kg and 30 mg (AHU377)/kg.

DSI remote pressure gauge was used to detect blood pressure and heart rate, and 28 days after administration, changes of systolic blood pressure and heart rate of SHRs were measured. The results are shown in Table 3 below.

TABLE 3

Antihypertensive and heart rate reduction effects in SHRs

| Group | systolic pressure change(mmHg) | heart rate change (times/minute) |
|---|---|---|
| normal control group | 3.2 ± 2.0 | 8.2 ± 3.3 |
| blank control group | 8.3 ± 5.4 | 10.1 ± 2.9 |
| Compound 1K group | −50.4 ± 4.7 | −29.3 ± 4.1 |
| valsartan group | −30.6 ± 3.5 | −10.6 ± 3.2 |
| Azilsartan kaMedoxoMil | −33.5 ± 3.2 | −11.1 ± 3.7 |
| AHU 377K group | −15.6 ± 2.5 | −8.1 ± 2.8 |
| AHU377 ammonium salt group | −18.5 ± 2.5 | 3 ± 2.1 |
| LCZ696 group | −52.4 ± 5.8 | −23.2 ± 4.3 |
| valsartan + AHU 377K group | −36.5 ± 4.2 | −16.2 ± 3.1 |
| Azilsartan kaMedoxoMil + AHU 377K group | −42.0 ± 3.4 | −14.4 ± 4.1 |
| Compound 1K + AHU 377K group | −65.7 ± 4.9 | −45.2 ± 5.3 |
| Compound 1K + AHU377 ammonium salt group | −60.3 ± 5.9 | −30 ± 1.5 |

As can be seen from the results in Table 3, the pharmaceutical composition of the present specification has a significant antihypertensive effect compared to any single component, as well as obvious improvement on the regulation of heart rate. It is also found in the experiment that synergistic technical effects were obtained by the application of the pharmaceutical compositions, with more stable blood pressure curve and long-lasting effect of blood pressure reduction and heart rate reduction. Therefore, the pharmaceutical compositions can be used at lower dose or lower frequency to achieve desired antihypertensive effect and reduce the side effects caused by employment of single drug.

Example 10. Therapeutic Effect of Pharmaceutical Composition on Chronic Heart Failure Rats Five-week-old male DSS rats (purchased from Beijing Weitong Lihua Experimental Animal Technology Co., Ltd.) were randomly divided into 10 groups, among which, one group were fed with low salt as normal control group and the other 9 groups were fed with high salt. The low-salt feeding group were administered 0.3% sodium chloride, and high-salt feeding group were administered 8% sodium chloride to induce hypertension-cardiac hypertrophy-heart failure to form pathological model. After continuous feeding 6-weeks-age rats for 5 weeks, administration was started at 11-weeks-age of the rats, and the dose administered to each group was the same as that in Example 8, continuously for 7 weeks. The rats were killed at 18-weeks-age for analysis of blood pressure and atrial natriuretic peptide (ANP). The results are shown in Table 4 below.

TABLE 4

Therapeutic effects of chronic heart failure in rats

| Group | systolic pressure change (mmHg) | ANP rate of change (%) |
|---|---|---|
| normal control group | 4.8 ± 5.5 | — |
| blank control group | 19.6 ± 3.2 | 107 ± 8 |
| Compound 1K group | −48.5 ± 7.5 | 158 ± 7 |
| valsartan group | −32.4 ± 4.6 | 125 ± 52 |
| Azilsartan kaMedoxoMil | −36.3sium | 132.3s |
| AHU 377K group | −20.6p7Km | 143.6p |
| AHU377 ammonium salt group | −18.3p am | 135.3p |
| LCZ696 group | −53.9p am | 201.9p |
| valsartan + AHU 377K group | −37.5rtan | 178.5 |
| Azilsartan kaMedoxoMil + AHU 377K group | −43.3 gro | 183.3 |
| Compound 1K + AHU 377K group | −66.3und | 235.3u |
| Compound 1K + AHU377 ammonium salt group | −60.9und | 228.9 |

It can be seen from the results in Table 4 that the pharmaceutical compositions of the present specification, compare to single drugs and other combinations, can significantly increase the secretion of ANP, improve the heart function of the rat, and make the blood pressure level closer to the normal level. The above data indicates that the composition has better curative effect for chronic heart failure, with synergistic effects.

Example 11. Therapeutic Effect of Pharmaceutical Compositions on Acute Heart Failure Caused by Coronary Artery Ligation Male Sprague-Dawley rats (purchased from Beijing Weitong Lihua Experimental Animal Technology Co., Ltd.) were used to perform heart failure model by coronary artery ligation (CAL). One week after surgery, the myocardial infarct size of the rats was examined by echocardiography. The infarct size ranged from 30% to 50% for successful modeling. Operations on the normal control group were the same as above, except for the absence of arterial ligation. Rats with successful modeling were randomly divided into 9 groups, wherein each group has 10 rats. Each group were administered the same dosage as in example 9. Cardiac function was detected by cardiac ultrasound after 4 weeks of continuous administration, and changes of mean arterial pressure (MAP) and left ventricular ejection fraction (EF) were analyzed. The results are shown in Table 5 below.

TABLE 5

Mean arterial pressure and left ventricular ejection fraction in rats with heart failure

| Group | MAP(mmHg) | EF(%) |
|---|---|---|
| normal control group | 135.8 ± 11.6 | 76.9 ± 9.5 |
| blank control group | 197.4 ± 10.2 | 30.5 ± 2.4 |
| Compound 1K group | 145.5 ± 8.9 | 48.6 ± 5.3 |
| valsartan group | 154.4 ± 4lsa | 35.3arta |
| Azilsartan kaMedoxoMil | 150.4sium | 45.14siu |
| AHU 377K group | 170.6p7K | 37.46p7K |
| AHU377 ammonium salt group | 172oup | 322oup |
| LCZ696 group | 142.3p amm | 58.23p a |
| valsartan + AHU 377K group | 156.5rtan+ | 49.55rta |
| Azilsartan kaMedoxoMil + AHU 377K group | 149.3 gro | 48.33 gr |
| Compound 1K + AHU 377K group | 134.3und 1 | 66.1 ± 5.8 |
| Compound 1K + AHU377 ammonium salt group | 146.3und | 62.63und |

It can be seen from the results in Table 5 that the pharmaceutical compositions of the present specification, compare to single drugs and other combinations, can significantly reduce the mean arterial pressure of animals with acute heart failure, improve the ejection fraction, and have a good therapeutic effect on acute heart failure caused by myocardial ischemia, with synergistic effect.

Example 12

The azilsartan medoxomil derivative, NEP inhibitor, lactose and microcrystalline cellulose were premixed for 5 min, stirred at 3 rpm, and cut at 30 rpm; Povidone was dissolved in an appropriate amount of water (calculated by 0.36 g povidone dissolved in 2 g water). Binder aqueous solution was added during stirring and cutting. The obtained soft material was granulated through a 30 mesh sieve, and then the wet granules were dried at 60° C. until the remaining moisture was 1%-2%. The granules were then sifted through a 24 mesh sieve, weighed, added with croscarmellose sodium and magnesium stearate, uniformly mixed, and tableted to form a tablet.

| Component | amount |
|---|---|
| Compound 1K | 20.0 mg |
| AHU 377K | 100.0 mg |
| Lactose | 100 mg |
| Microcrystalline cellulose | 10 mg |
| Povidone | 3.6 mg |
| Croscarmellose sodium | 15 mg |
| Magnesium stearate | 2 mg. |

Example 13

The azilsartan medoxomil derivative, NEP inhibitor, dioleoylphosphatidylcholine, cholesterol, sodium glycocholate and soybean sterol were dissolved in a mixed solvent of ethanol and n-hexane, uniformly mixed, and evaporated under reduced pressure in a rotating thin film evaporator for removal of organic solvent to obtain a phospholipid membrane, which was then added with a buffer solution of citric acid-sodium citrate at pH of 6.0, shaken, and stirred for 30 minutes for complete hydration of the phospholipid membrane, emulsified by a tissue masher at a high speed for 10 minutes, and filtered by a 0.45 μm microporous membrane to prepare a liposome suspension. The suspension was spray-dried to obtain a drug-containing liposome powder, which was then mixed with mannitol, microcrystalline cellulose and croscarmellose sodium, sifted by a 60 mesh sieve while mixed evenly, added with hydroxypropyl cellulose and ethanol solution to make soft material. The soft material was sifted by a 20 mesh sieve for granulation, dried at 50° C., mixed with dry particles and magnesium stearate evenly, granulated through a 18 mesh sieve, compressed, and coated to obtain liposome tablets.

| Component | amount |
|---|---|
| Compound 1K | 20 mg |
| AHU 377 Na | 40 mg |
| Dioleoylphosphatidylcholine | 180 mg |
| Cholesterol | 38 mg |
| Sodium glycocholate | 50 mg |
| Soyasterol | 15 mg |
| Mannitol | 60 mg |
| Microcrystalline cellulose | 180 mg |
| Croscarmellose sodium | 30 mg |
| Hydroxypropyl cellulose | 5 mg |
| Magnesium stearate | 6 mg. |

Example 14

Materials were firstly sieved for use. Azilsartan medoxomil derivative, NEP inhibitor, mannitol and croscarmellose sodium were poured into a three-dimensional mixer for 5 min, stirred at 3 rpm, cut at 30 rpm; and then added with calcium stearate while mixed evenly. The total mixed materials were tableted in a rotary tableting machine.

| component | amount |
|---|---|
| Compound 1K | 40 mg |
| AHU 377K | 60 mg |
| Mannitol | 108 mg |
| Croscarmellose sodium | 15 mg |
| Calcium stearate | 5 mg. |

Example 15

Materials were firstly sieved for use. Azilsartan medoxomil derivative, NEP inhibitor, mannitol-starch and crospovidone were pre-mixed for 5 min, stirred at 3 rpm, cut at 30 rpm; granulated in a dry granulator and mixed in a three-dimensional mixer after magnesium stearate was added. The total mixed materials were tableted in a rotary tableting machine.

| component | amount |
|---|---|
| Compound 1K | 10 mg |
| AHU 377K | 100 mg |
| Mannitol-starch | 100 mg |
| crospovidone | 15 mg |
| magnesium stearate | 5 mg |

Example 16

Materials were firstly sieved for use. Azilsartan medoxomil derivative, NEP inhibitor, lactose and croscarmellose sodium were premixed for 5 min, stirred at 3 rpm, and cut at 30 rpm, added with a binder aqueous solution which was prepared by povidone dissolved in an appropriate amount of water (5% solution), granulated, dried in fluidized bed. The dried granules were mixed in a three-dimensional mixer, with magnesium stearate. The total mixed materials were tableted in a rotary tableting machine.

| Component | amount |
|---|---|
| Compound 1K | 40 mg |
| AHU 377K | 50 mg |
| Lactose | 150 mg |
| Croscarmellose sodium | 15 mg |
| Povidone | 10 mg |
| Magnesium stearate | 5 mg |

Example 17

Materials were firstly sieved for use. Azilsartan medoxomil derivative, NEP inhibitor, microcrystalline cellulose 101, crospovidone, and talc powder were premixed for 5 min, stirred at 3 rpm, cut at 30 rpm, and granulated in a dry granulator. The granules were placed in a three-dimensional mixer and mixed with microcrystalline cellulose 102 and magnesium stearate. The total mixed materials were tableted in a rotary tableting machine.

Example 18

Materials were sieved for use. Azilsartan medoxomil derivative, NEP inhibitor, mannitol, and croscarmellose sodium were poured into a three-dimensional mixer for 5 min, stirred at 3 rpm, cut at 30 rpm; and then mixed with calcium stearate evenly. The total mixed materials were tableted in a rotary tableting machine.

| Component | amount |
|---|---|
| Compound 1K | 40 mg |
| AHU 377 ammonium salt | 60 mg |
| Mannitol | 108 mg |
| Croscarmellose sodium | 15 mg |
| Calcium stearate | 5 mg. |

The exemplary embodiments of the present invention have been described above. However, the present invention is not limited thereto. Any modification, equivalent substitution and improvement, etc., which are made within the spirit and scope of the invention, should fall within the scope of the invention.

What is claimed is:

1. A pharmaceutical composition comprising:
    (a) at least one neutral endopeptidase inhibitor selected from sodium 4-(((2S,4R)-1-([1,1'-biphenyl]-4-yl)-5-ethoxy-4-methyl-5-oxopentan-2-yl) amino)-4-oxobutyrate,
    potassium 4-(((2S,4R)-1-([1,1'-biphenyl]-4-yl)-5-ethoxy-4-methyl-5-oxopentan-2-yl) amino)-4-oxobutanoate, and
    ammonium 4-(((2S,4R)-1-([1,1'-biphenyl]-4-yl)-5-ethoxy-4-methyl-5-oxopentan-2-yl) amino)-4-oxobutanoate;
    (b) a compound of formula (1K);

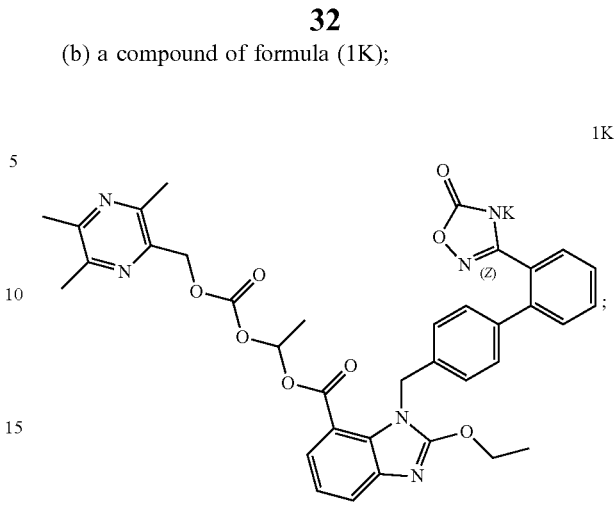

and
    a pharmaceutically acceptable carrier.

2. A pharmaceutical kit comprising separate containers, wherein a first container of the containers comprises:
    (a) a first pharmaceutical composition comprising a first pharmaceutically acceptable carrier, and at least one neutral endopeptidase inhibitor defined as in claim 1;
    and a second container of the containers comprises:
    (b) a second pharmaceutical composition comprising a second pharmaceutically acceptable carrier, and the compound of formula (1K) defined as in claim 1.

3. The pharmaceutical composition according to claim 1, wherein a mass ratio of the at least one neutral endopeptidase inhibitor to the compound of formula (1K) is (0.5-10) : 1.

4. (Withdrawn and Previously Presented) A medicament comprising the pharmaceutical composition according to claim 1.

5. A method for preparing the medicament of claim 4, comprising combining
    (a) the at least one neutral endopeptidase inhibitor;
    (b) the compound of formula (1K); and
    the pharmaceutically acceptable carrier.

6. The pharmaceutical composition according to claim 1, wherein the compound of formula (1K) is selected from at least one of the group consisting of an amorphous, crystalline form I, crystalline form II, crystalline form III, and crystalline form IV of the compound of formula(1K).

7. The pharmaceutical kit according to claim 2, wherein a mass ratio of the (a) to the (b) is (0.5-10) : 1.

8. A method for treating a cardiovascular disease, comprising: administering the pharmaceutical composition according to claim 1 to a subject in need thereof.

9. The method according to claim 8, wherein the cardiovascular disease is selected from the group consisting of hypertension, heart failure, coronary heart disease, rheumatic heart disease, congenital heart disease, left ventricular dysfunction, endothelium dysfunction, diastolic dysfunction, hypertrophic cardiomyopathy, diabetic cardiomyopathy, supraventricular and ventricular arrhythmia, atrial fibrillation, cardiac fibrosis, atrial flutter, harmful vascular remodeling, myocardial infarction and its sequelae, arteries atherosclerosis, angina pectoris, primary and secondary pulmonary hypertension, and renal vascular hypertension.

10. The pharmaceutical composition according to claim 6, wherein the compound of formula (1K) is the crystalline form I, the crystalline form II or a mixture of the crystalline form I and the crystalline form II in any ratio.

11. The pharmaceutical composition according to claim 1, wherein a mass ratio of the at least one neutral endopeptidase inhibitor to the compound of formula (1K) is (0.5-5) : 1.

12. A method for treating a cardiovascular disease, comprising: administering the pharmaceutical kit according to claim 2 to a subject in need thereof.

13. The method according to claim 12, wherein a mass ratio of the first pharmaceutical composition to the second pharmaceutical composition is (0.5-10):1.

* * * * *